US012219966B2

(12) United States Patent
Pettersen et al.

(10) Patent No.: US 12,219,966 B2
(45) Date of Patent: Feb. 11, 2025

(54) LIVE FISH PROCESSING SYSTEM, AND ASSOCIATED METHODS

(71) Applicant: Pharmaq AS, Overhalla (NO)

(72) Inventors: Jorn Stale Pettersen, Nesna (NO); Remy Kristian Oddoy, Nesna (NO); Johan Odd Moflag, Nesna (NO); Steffen Langseth, Nesna (NO)

(73) Assignee: Pharmaq AS, Overhalla (NO)

( * ) Notice: Subject to any disclaimer, the term of this patent is extended or adjusted under 35 U.S.C. 154(b) by 266 days.

(21) Appl. No.: 16/055,296

(22) Filed: Aug. 6, 2018

(65) Prior Publication Data

US 2019/0037865 A1 Feb. 7, 2019

Related U.S. Application Data

(60) Provisional application No. 62/541,917, filed on Aug. 7, 2017.

(51) Int. Cl.
*A01K 61/10* (2017.01)
*A01K 61/13* (2017.01)
(Continued)

(52) U.S. Cl.
CPC .............. *A22C 25/08* (2013.01); *A01K 61/10* (2017.01); *A01K 61/13* (2017.01); *A01K 61/95* (2017.01);
(Continued)

(58) Field of Classification Search
CPC ........ A01K 61/10; A01K 61/90; A01K 61/95; A01K 61/13; A22C 25/08
(Continued)

(56) References Cited

U.S. PATENT DOCUMENTS

| 4,934,537 A | 6/1990 | DeBourke |
| 5,103,767 A | 4/1992 | Haugland et al. |

(Continued)

FOREIGN PATENT DOCUMENTS

| AU | 2016354512 | 5/2017 |
| CN | 1033732 A | 7/1989 |

(Continued)

OTHER PUBLICATIONS

PCT Search Report, International Application No. PCT/US2018/045353, International Filing Date Aug. 6, 2018, Date of mailing Jan. 8, 2019.

(Continued)

*Primary Examiner* — David J Parsley
(74) *Attorney, Agent, or Firm* — Scott C. Mayhew

(57) ABSTRACT

A fish handling unit for processing live fish is provided. Such fish handling unit includes an inspection system configured to inspect a plurality of live fish. A conveyor assembly transports the live fish to the inspection system. At least one robotic cell is in communication with the inspection system. The robotic cell has a controller configured to control operation thereof. An end effector is operably engaged with the robotic cell. The end effector interacts with the live fish moving along the conveyor assembly, based on information determined by the inspection system and received by the controller. The end effector may optionally be an integrated gripper and injection assembly capable of orientation and injection of the live fish. Associated devices and methods are also provided.

5 Claims, 20 Drawing Sheets

(51) Int. Cl.
- *A01K 61/95* (2017.01)
- *A22C 25/08* (2006.01)
- *G01N 33/12* (2006.01)
- *G06T 7/00* (2017.01)
- *B65G 47/90* (2006.01)

(52) U.S. Cl.
CPC ........... *G01N 33/12* (2013.01); *G06T 7/0004* (2013.01); *B65G 47/90* (2013.01); *G06T 2207/30128* (2013.01)

(58) Field of Classification Search
USPC .......... 119/201, 216, 203; 452/53, 180, 181, 452/184
See application file for complete search history.

(56) References Cited

U.S. PATENT DOCUMENTS

| | | | | |
|---|---|---|---|---|
| 5,215,035 A | * | 6/1993 | Rod | A01K 61/90 119/201 |
| 6,145,476 A | * | 11/2000 | Tempel | A22B 3/083 119/215 |
| 6,286,460 B1 | * | 9/2001 | Gudbjornsson | A01K 61/90 119/200 |
| 6,532,064 B1 | | 3/2003 | Hearn et al. | |
| 7,841,300 B2 | * | 11/2010 | Skvorc, II | A01K 29/00 119/712 |
| 8,047,093 B2 | | 11/2011 | Kinoshita et al. | |
| 8,092,283 B2 | * | 1/2012 | Hansen | A22C 25/142 452/121 |
| 8,109,173 B2 | | 2/2012 | Kinoshita et al. | |
| 2006/0081192 A1 | * | 4/2006 | Massey | A01K 61/90 119/215 |
| 2011/0207388 A1 | | 8/2011 | Hansen | |
| 2014/0197652 A1 | * | 7/2014 | Wang | B25J 15/0616 294/185 |

FOREIGN PATENT DOCUMENTS

| | | |
|---|---|---|
| CN | 2146118 Y | 11/1993 |
| CN | 201479735 U | 5/2010 |
| CN | 102601797 A | 7/2012 |
| CN | 102907363 | 2/2013 |
| CN | 104367396 A | 2/2015 |
| DE | 102007031847 * | 10/2008 |
| EP | 2551222 A1 | 1/2013 |
| FR | 2613185 A1 | 10/1988 |
| GB | 1518267 | 7/1978 |
| JP | 6046709 A2 | 2/1994 |
| JP | 2001 112795 A2 | 4/2001 |
| JP | 2003 159265 A2 | 6/2003 |
| JP | 2009-195173 A2 | 9/2009 |
| JP | 2010 179075 A2 | 8/2010 |
| NO | 20100912 | 12/2011 |
| NO | 343355 B1 | 2/2019 |
| RU | 2018223 C1 | 8/1994 |
| RU | 2016114629 | 10/2017 |
| RU | 2 645 979 C2 | 2/2018 |
| WO | WO 89/04601 | 6/1989 |
| WO | WO 94/09920 A1 | 5/1994 |
| WO | WO 99/00306 A2 | 1/1999 |
| WO | WO 03/069987 A1 | 8/2003 |
| WO | WO 2007/138616 * | 12/2007 |
| WO | WO 2009/007053 A1 | 1/2009 |
| WO | WO 2012/008843 A1 | 1/2012 |
| WO | WO 2017/083674 * | 5/2017 |

OTHER PUBLICATIONS

PCT Written Opinion, International Application No. PCT/US2018/045353, International Filing Date Aug. 6, 2018, Date of mailing Jan. 8, 2019.

Chilean Patent Office Action, Chilean Patent Application No. 202000325, dated Mar. 8, 2021, Non-English.

EPC Annex to the Communication dated Mar. 15, 2021, application No. EP18 768 989.8.

Russian Patent Search Report, Russian patent application No. 2020101926/10, Date of actual completion of the search: Aug. 31, 2020.

Chinese Patent Office Action, Chinese Patent Application No. 201880051441.0, dated May 21, 2021. Non-English.

Reporting letter of First Official Action of Chinese Patent Application No. 201880051441.0, dated Jun. 21, 2021.

Introduction to Mechanical Engineering, pp. 5.3.1-5.4, Non-English.

IP Office of Singapore Search Report, Singapore Patent Application No. 11202001085Q, Date of actual completion of the search: Dec. 3, 2021.

IP Office of Singapore Written Opinion, Singapore Application No. 11202001085Q, Date of actual completion of the search: Dec. 3, 2021.

Video: Maskon Vaccination machine for salmon. Nov. 14, 2013. Recuperado de: https://www.youtube.com/watch?v=RH6sbT6QPS8 el Nov. 9, 2021.

Brochure: Maskon vaccination system. Aug. 14, 2013. Recuperado de: https://en.skalamaskon.no/aquaculture2/vaccination/brocure-high-speedvaccination el Nov. 9, 2021.

Página web: Skala-Maskon—High Speed Fish Vaccination Machine. Aug. 11, 2015. Recuperado de: https://www.agriculture-xprt.com/products/skala-maskon-highspeed-fish-vaccination-machine-362803 el Nov. 9, 2021.

Brochure NFT Vaccination Machines Pharmaq Fishteq. Sep. 20, 2019. Recuperado de: https://www.pharmaq.com/media/yxbbk2ay/2019_nft-20-august-2019_web.pdf el Nov. 9, 2021.

Colombia Patent Office Action and Search Report, Colombia Patent Application No. NC2020/0001249, dated Oct. 20, 2021, Non-English.

Japanese Patent Office Action, Japanese Patent Application No. 2020-504381, of Mar. 28, 2022, Non-English.

Japanese Patent Office Action, Japanese Patent Application No. 2020-504381, of Mar. 28, 2022, English Translation.

* cited by examiner

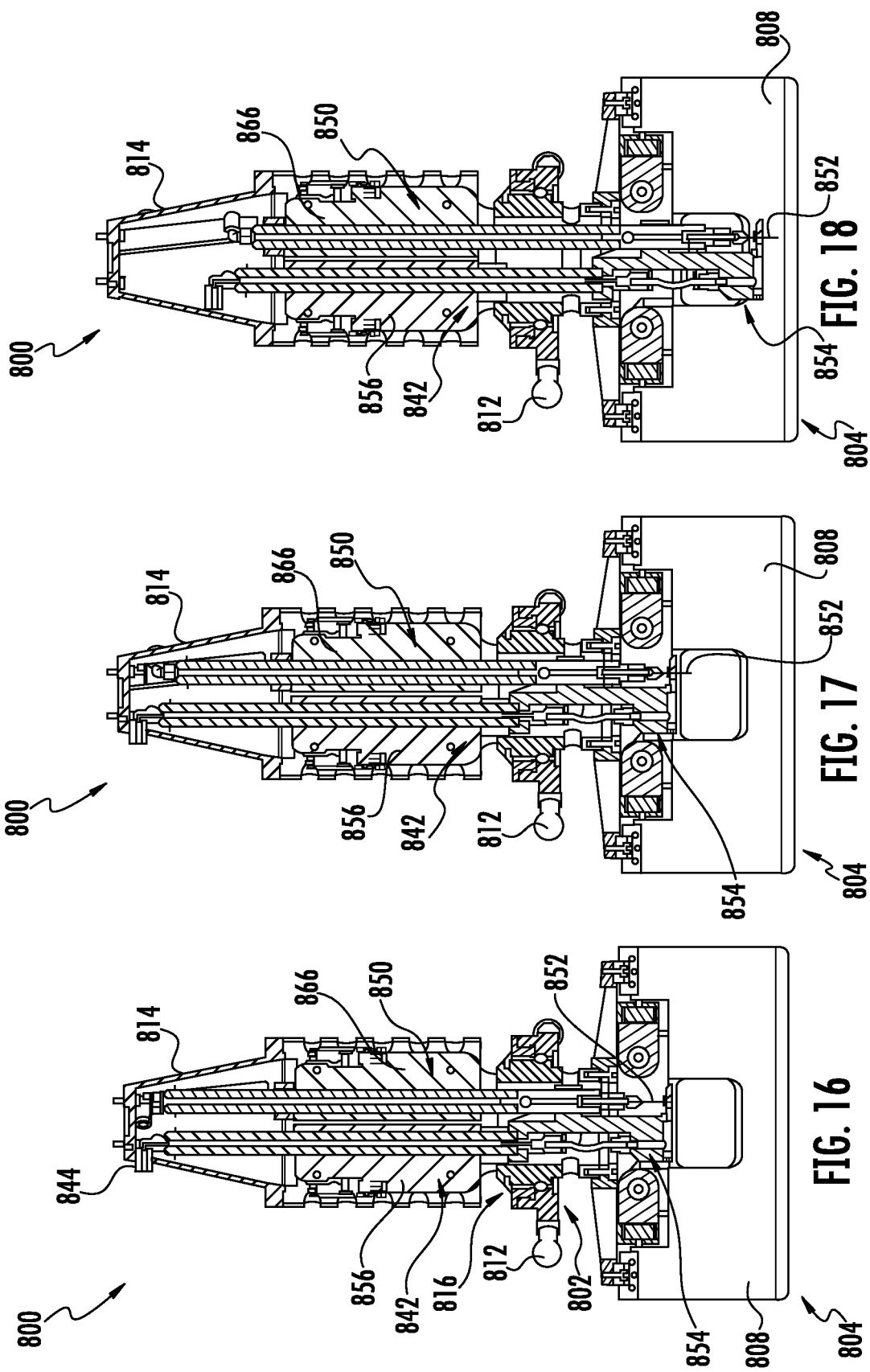

LIVE FISH PROCESSING SYSTEM, AND ASSOCIATED METHODS

CROSS REFERENCE TO RELATED APPLICATION

This application claims the benefit of U.S. Provisional Patent Application No. 62/541,917, filed Aug. 7, 2017, which is expressly incorporated herein by reference in its entirety.

TECHNICAL FIELD

The present disclosure generally relates to live fish processing systems and sub-systems. More particularly, the present disclosure relates to sub-systems implementing one or more robotic cells for automated processing of live fish, and associated methods.

BACKGROUND

Vaccination of live fish is performed completely manually or using semi-automatic or fully automatic machines. Operators inject a vaccine into each individual fish by means of a vaccination syringe or feed fish into a semi-automatic vaccination machine in a predetermined orientation. In the instance of fully automatic machines, the fish must be sorted and oriented upstream of an automated vaccination device such that the abdomen is accessible for targeted injection. Unfortunately, current upstream orienting sub-systems are physically challenging to the fish and also require a large footprint in the fish hatchery.

Accordingly, it would be desirable to provide a fish processing system capable of eliminating such orientating sub-systems such that less physical stress is demanded on the live fish, while reducing the overall footprint of the fish processing system. Furthermore, it would be desirable to provide associated methods to improve live fish processing and handling in the hatchery.

BRIEF SUMMARY

The above and other needs are met by aspects of the present disclosure which, according to one aspect, provides a fish handling unit having an inspection system configured to inspect a plurality of live fish. A conveyor assembly is configured to transport the live fish to the inspection system. The fish handling unit includes at least one robotic cell having a controller configured to control operation thereof, the controller being in communication with the inspection system. An end effector is operably engaged with the robotic cell. The end effector is configured to interact with the live fish moving along the conveyor assembly, based on information determined by the inspection system and received by the controller.

Another aspect provides a method of processing live fish. The method includes sedating a plurality of live fish. The live fish are conveyed to an inspection system. The live fish are inspected with the inspection system to determine information about each live fish. The information about the inspected fish is communicated to a robotic cell having an end effector operably engaged therewith and configured to interact with the live fish while conveyed. The live fish are processed by the end effector.

Still yet another aspect provides an inspection system for inspecting live fish. A conveyor assembly is segmented to provide a gap therein. A first image capture device is positioned on a side of the conveyor assembly, the first image capture device being configured to optically scan a first side of the live fish while transported along the conveyor assembly. A second image capture device is positioned on the opposite side of the conveyor assembly with respect to the first image capture device. The second image capture device is positioned proximate to the gap, and the second image capture device is configured to capture through the gap a plurality of images of a second side of the live fish, opposite the first side, while the live fish are transported along the conveyor assembly. A processor is configured to construct a visual image of the second side of the live fish using the images captured by the second image capture device.

Thus, various aspects of the present disclosure provide advantages, as otherwise detailed herein.

BRIEF DESCRIPTION OF THE DRAWINGS

Figure 1:
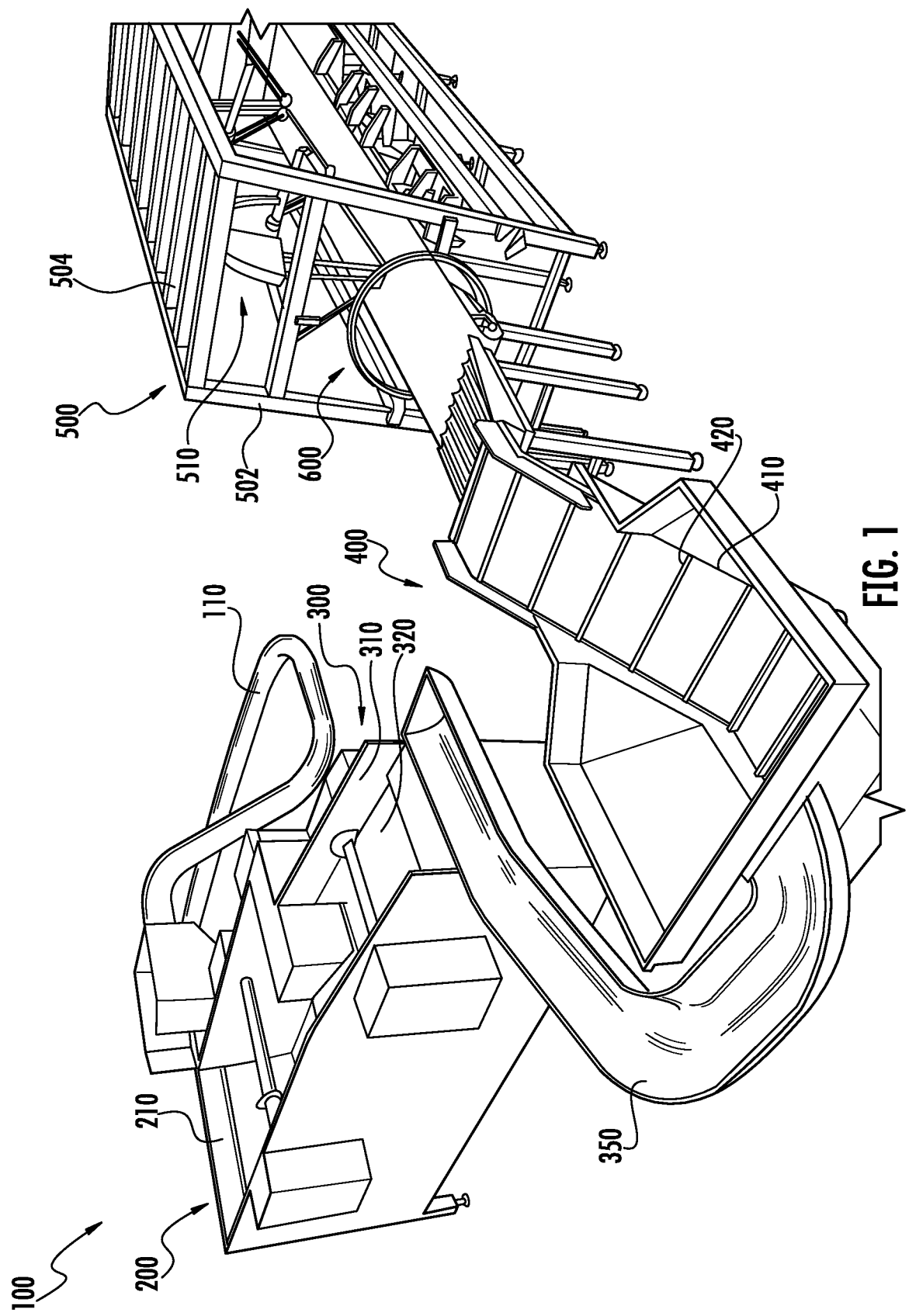
Figure 2:
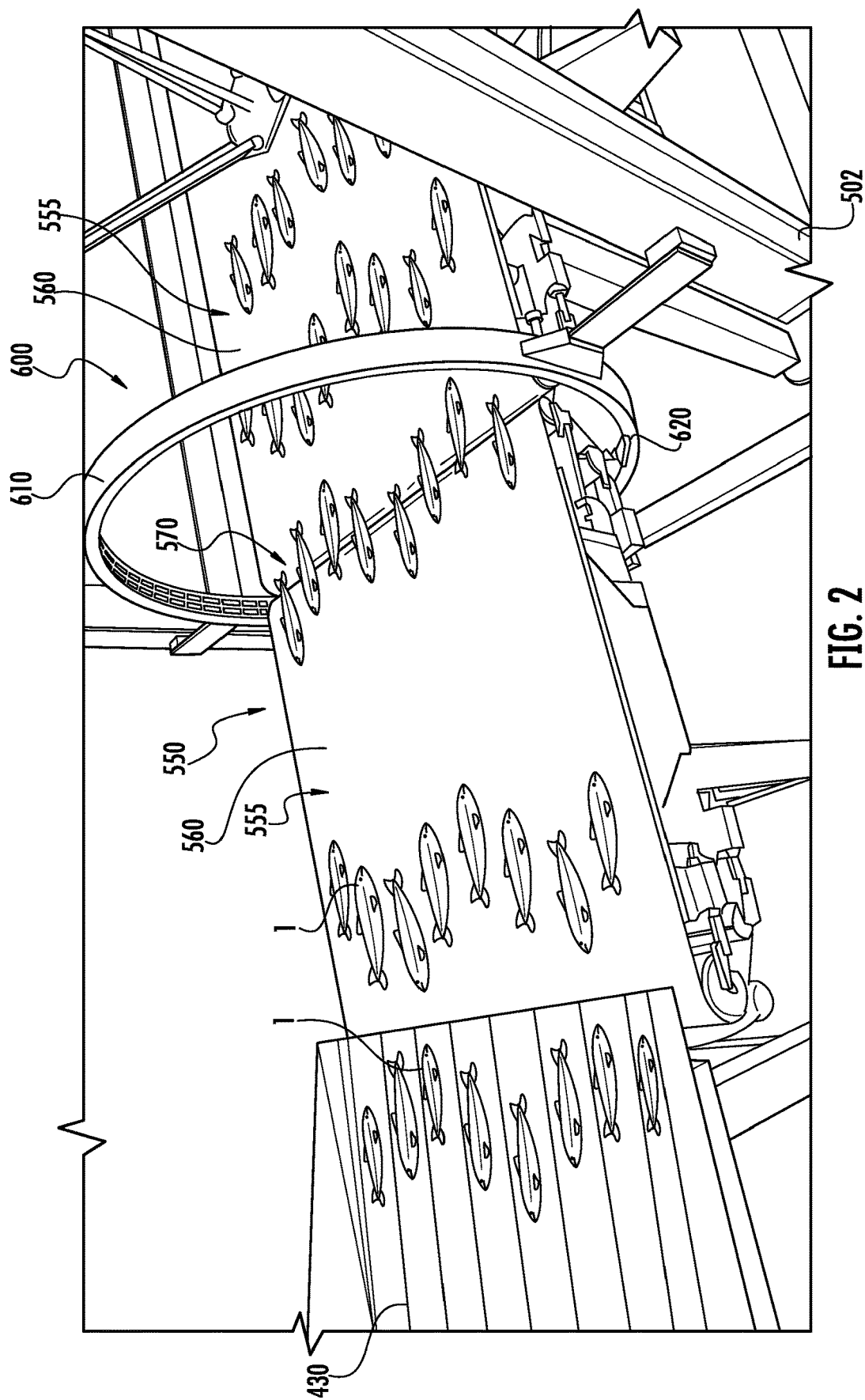
Figure 3:
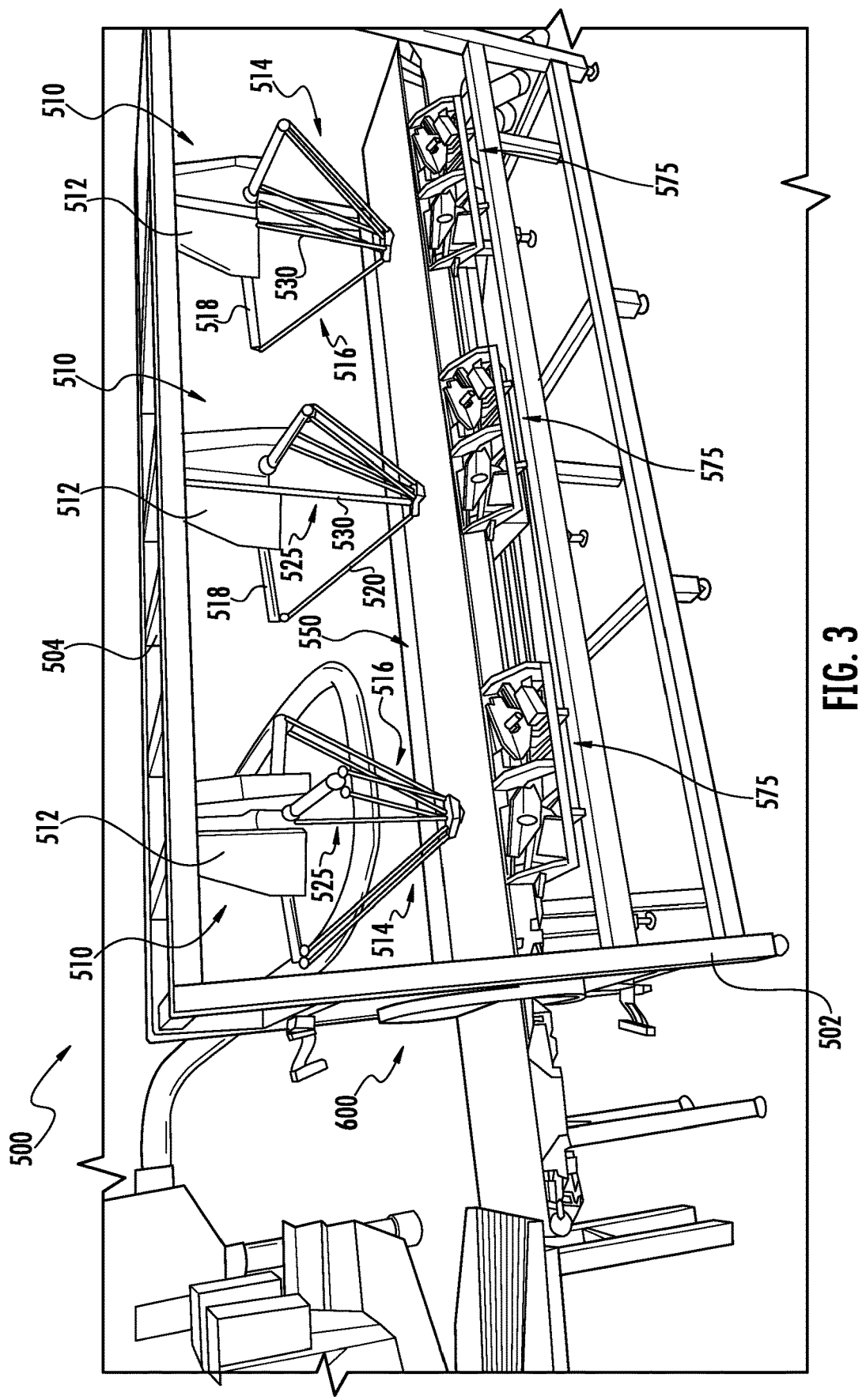
Figure 4:
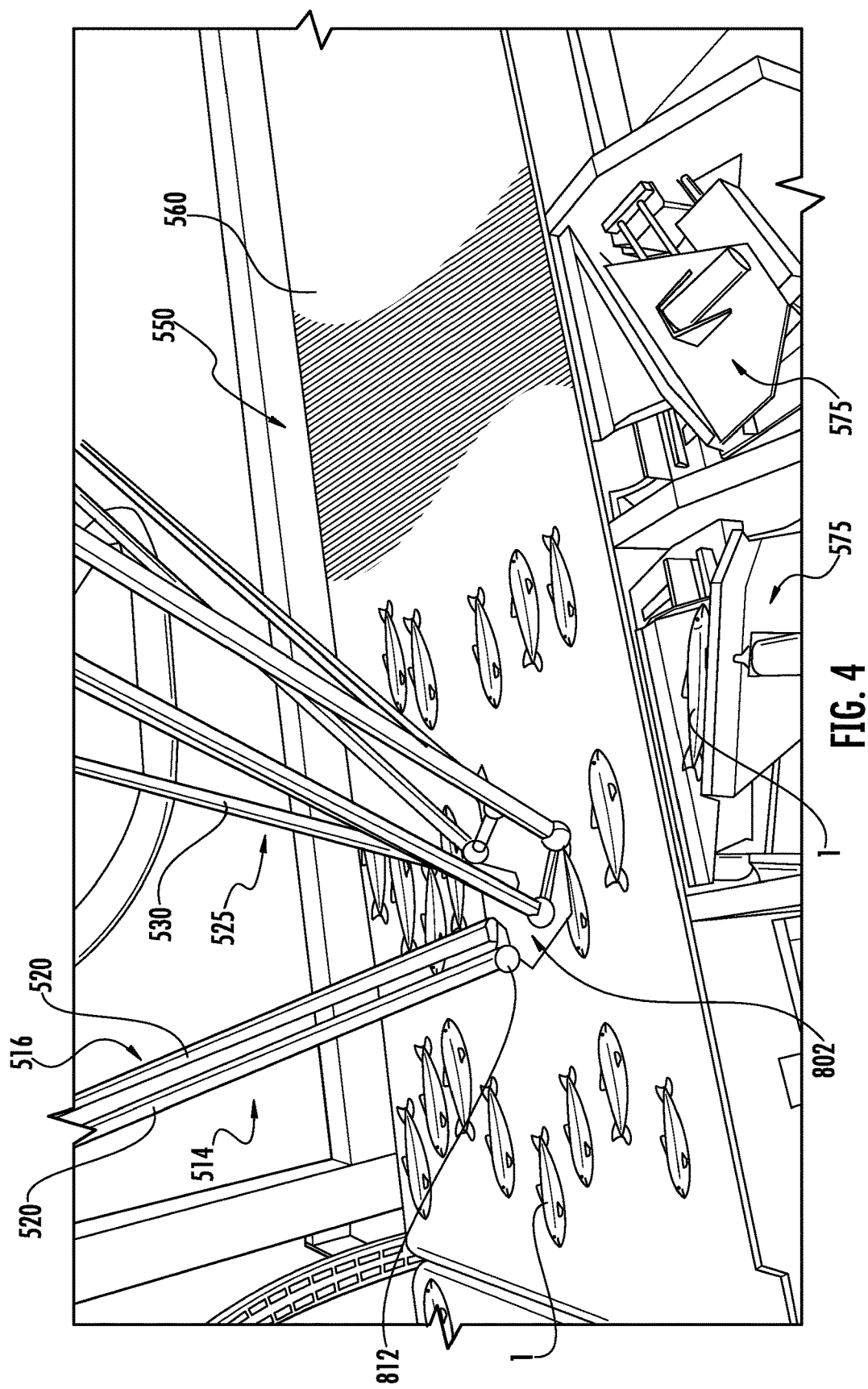
Figure 5:
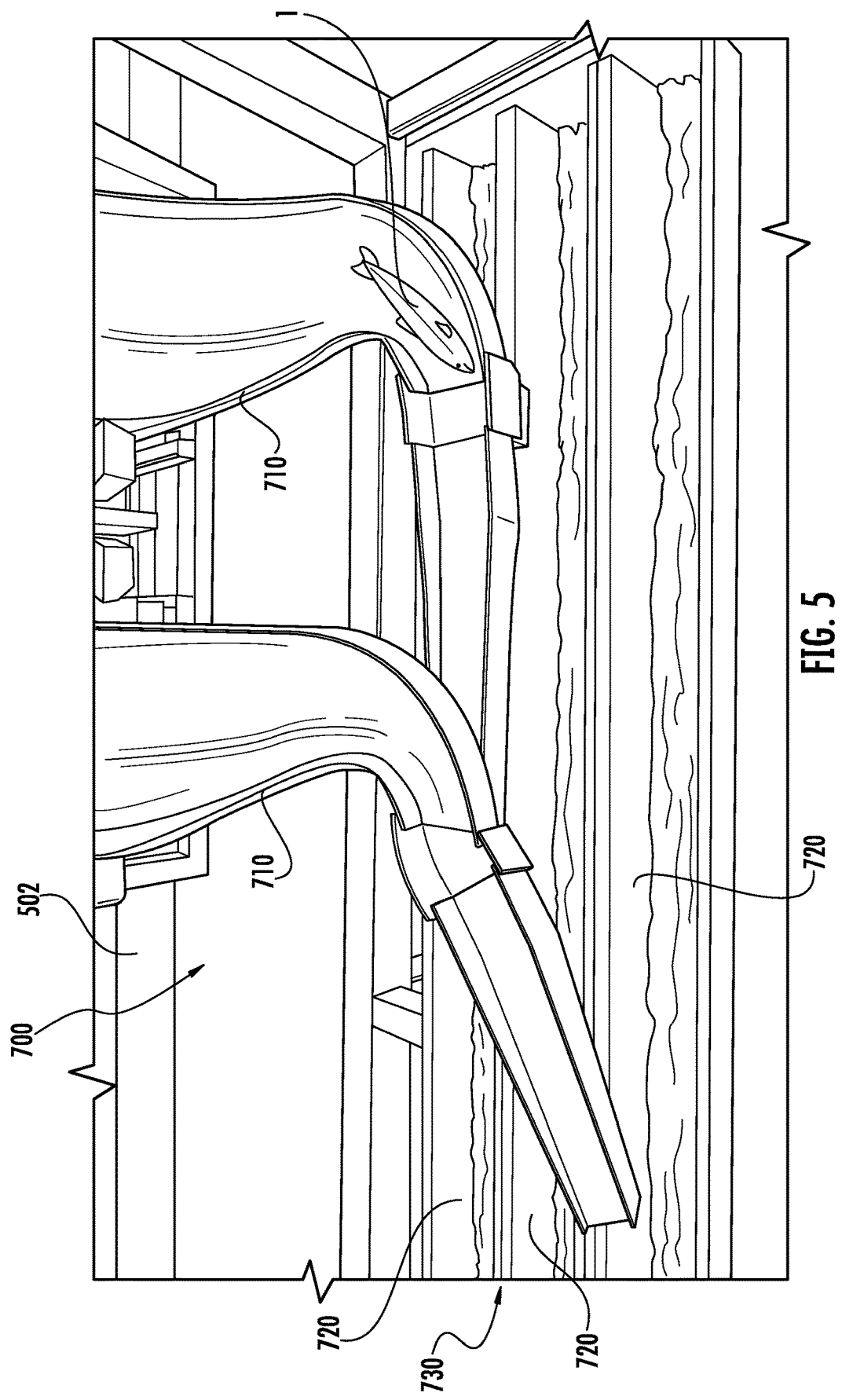
Figure 6:
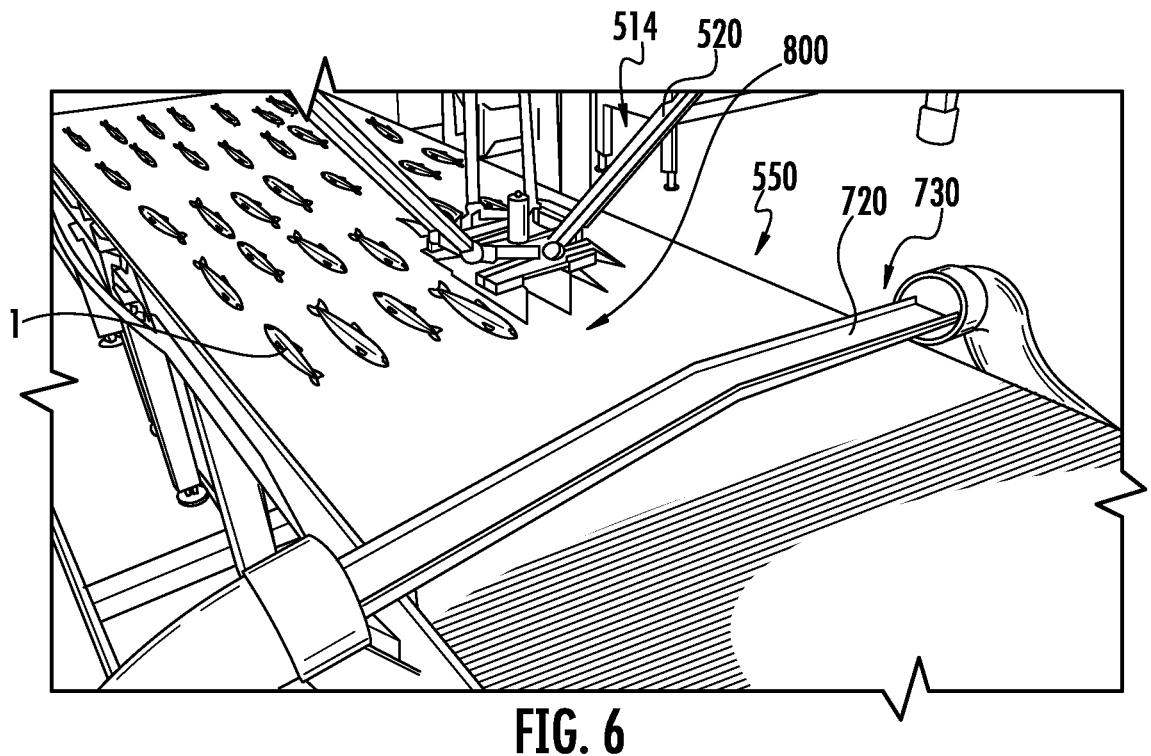
Figure 7:
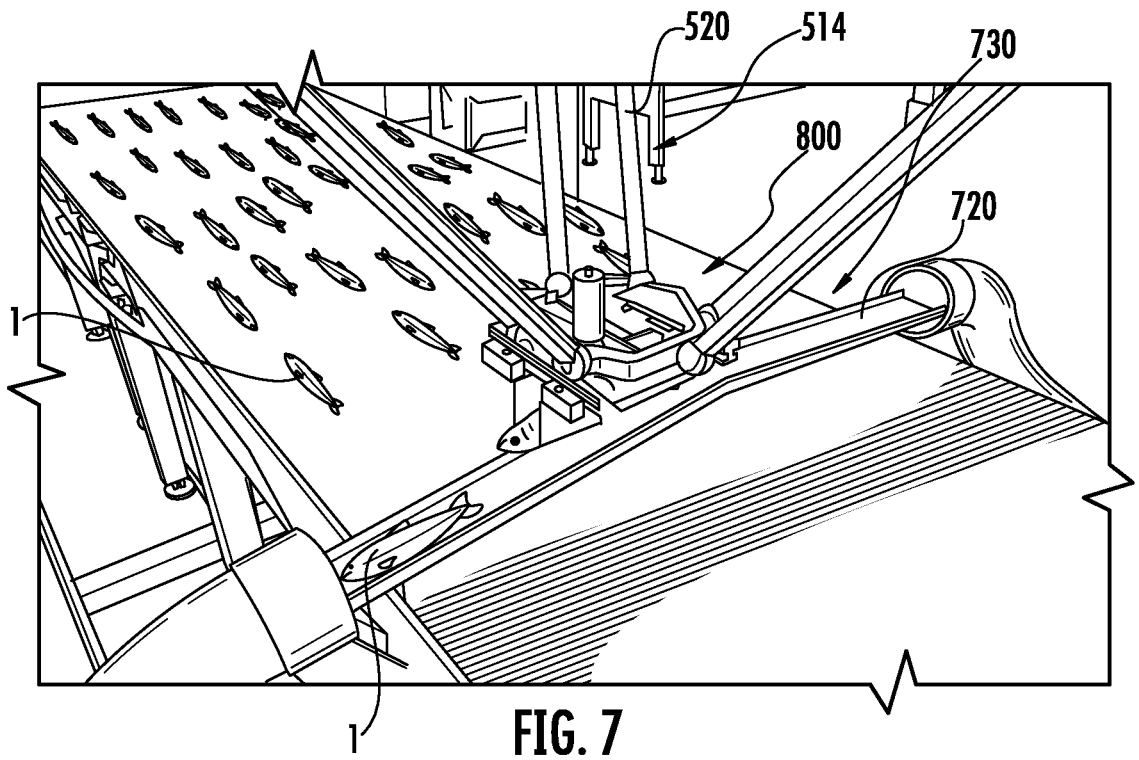
Figure 8:
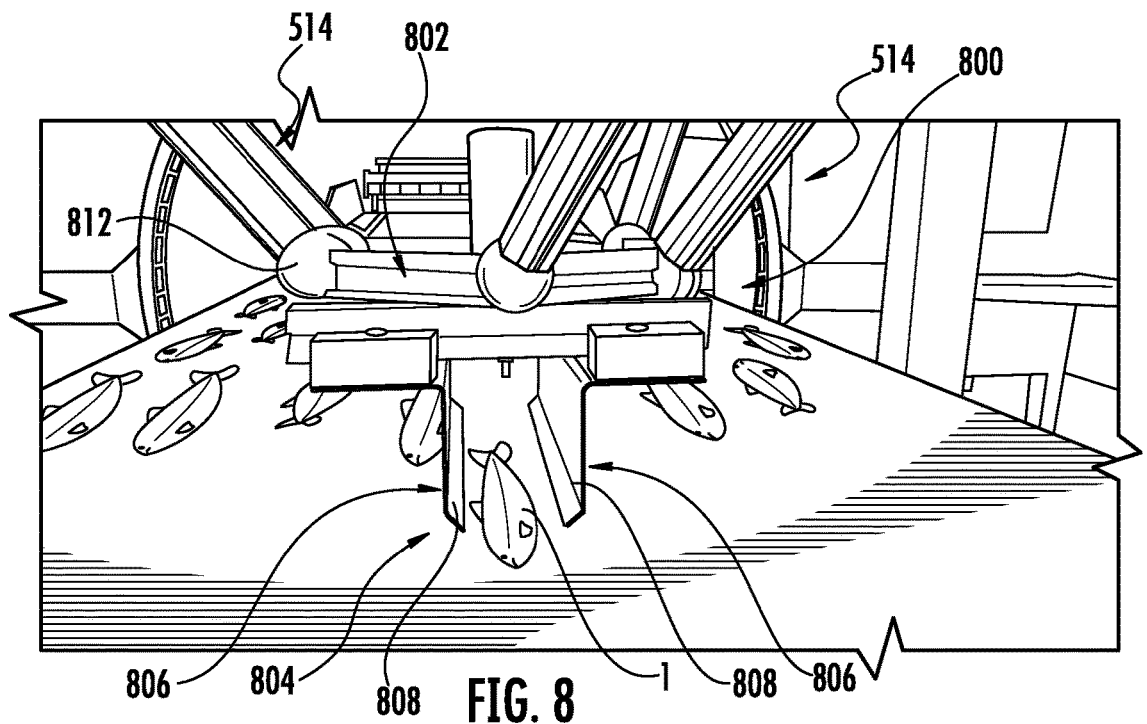
Figure 9:
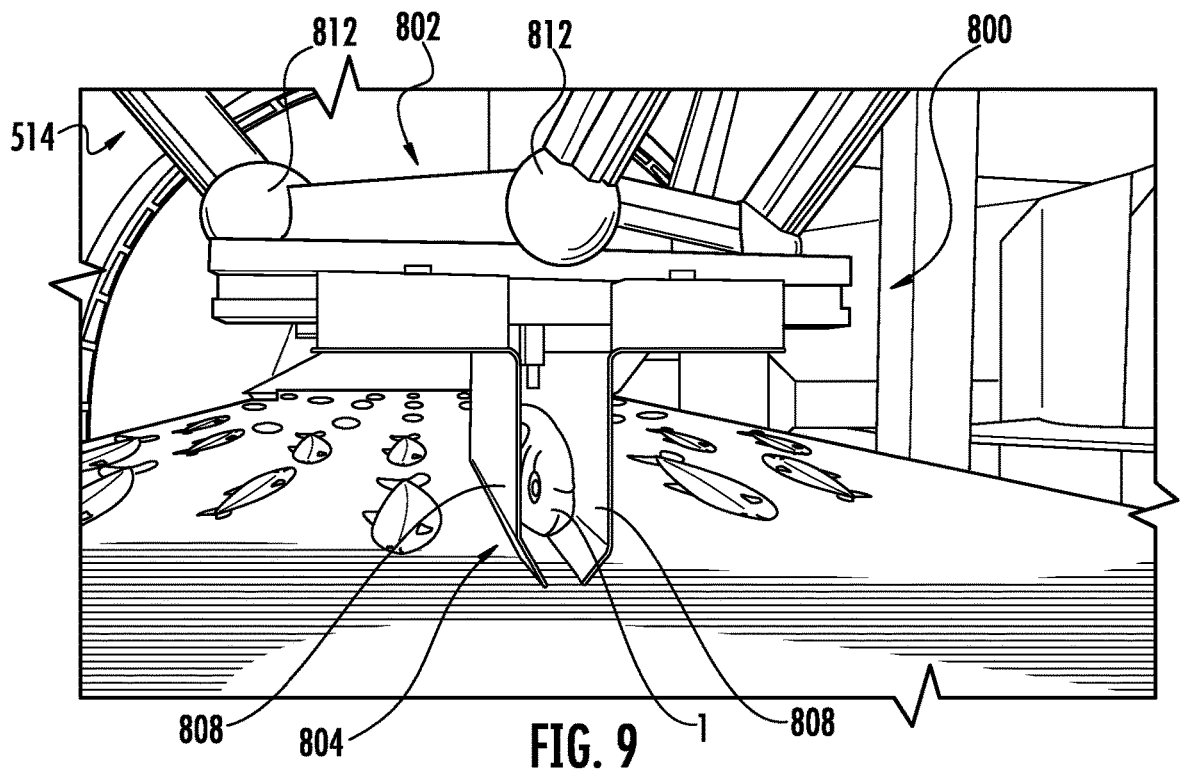
Figure 10:
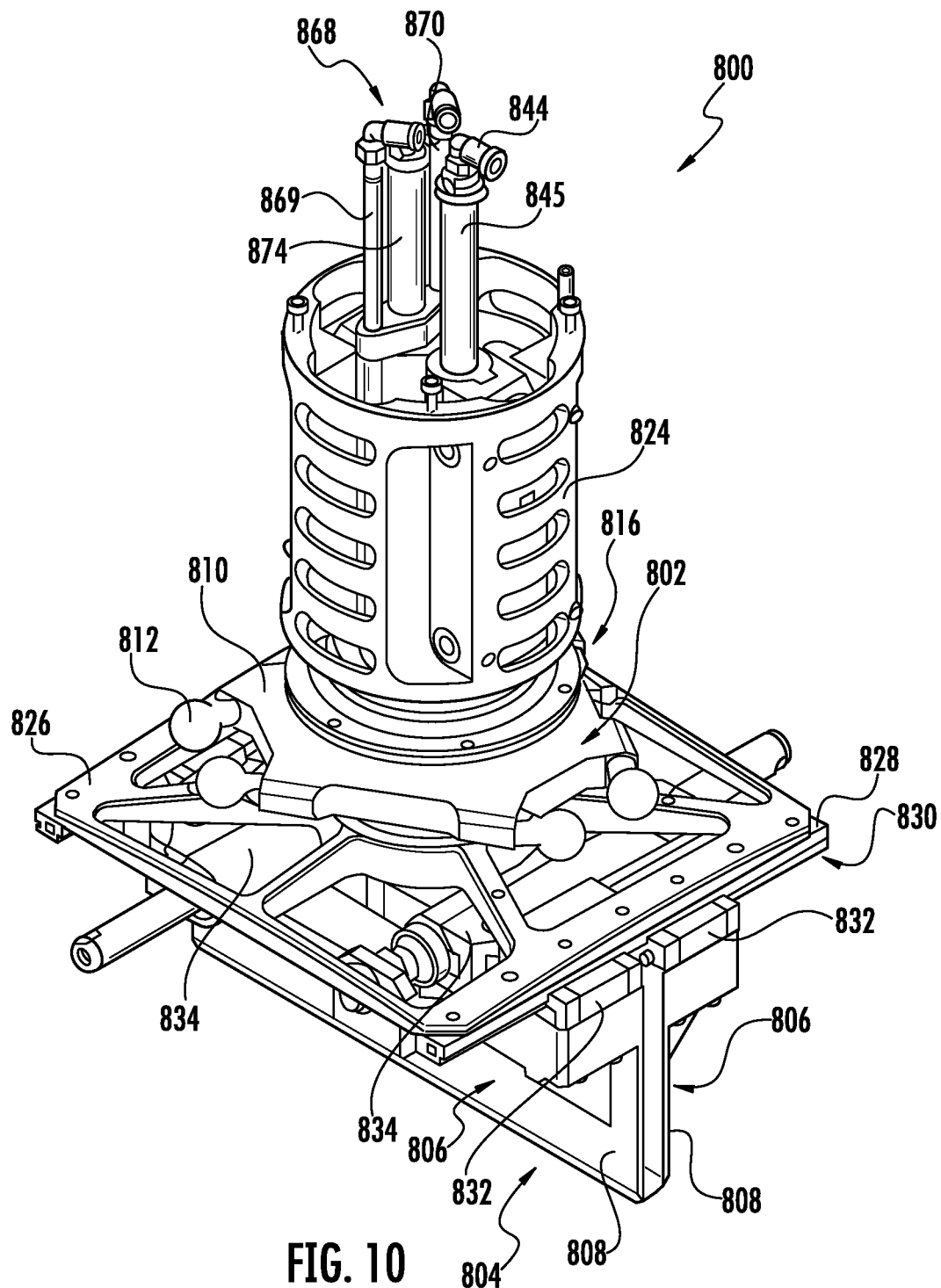
Figure 12:
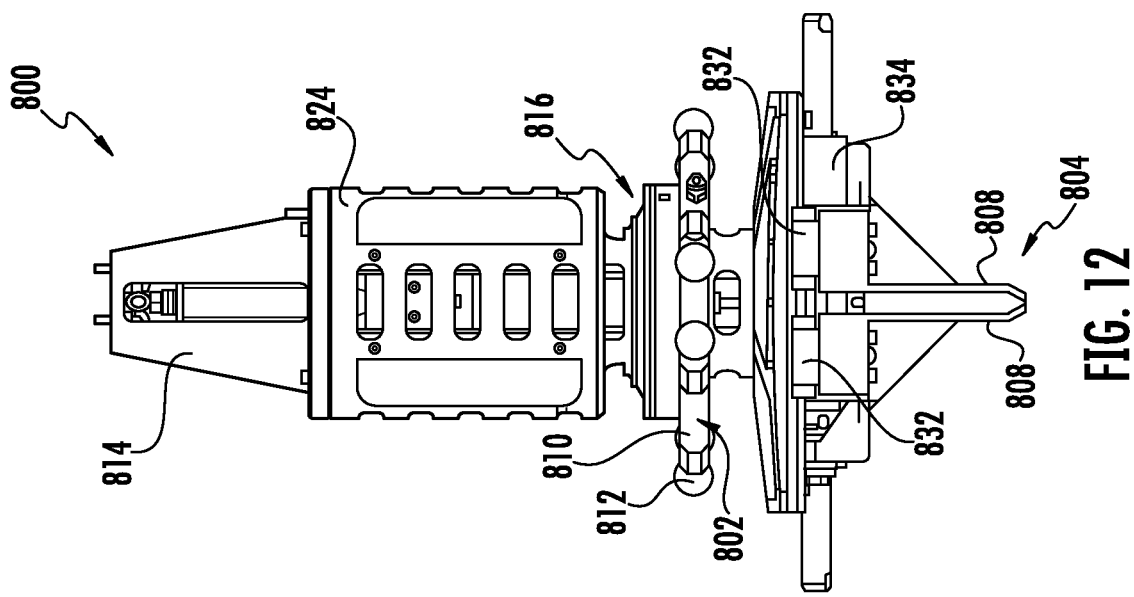
Figure 11:
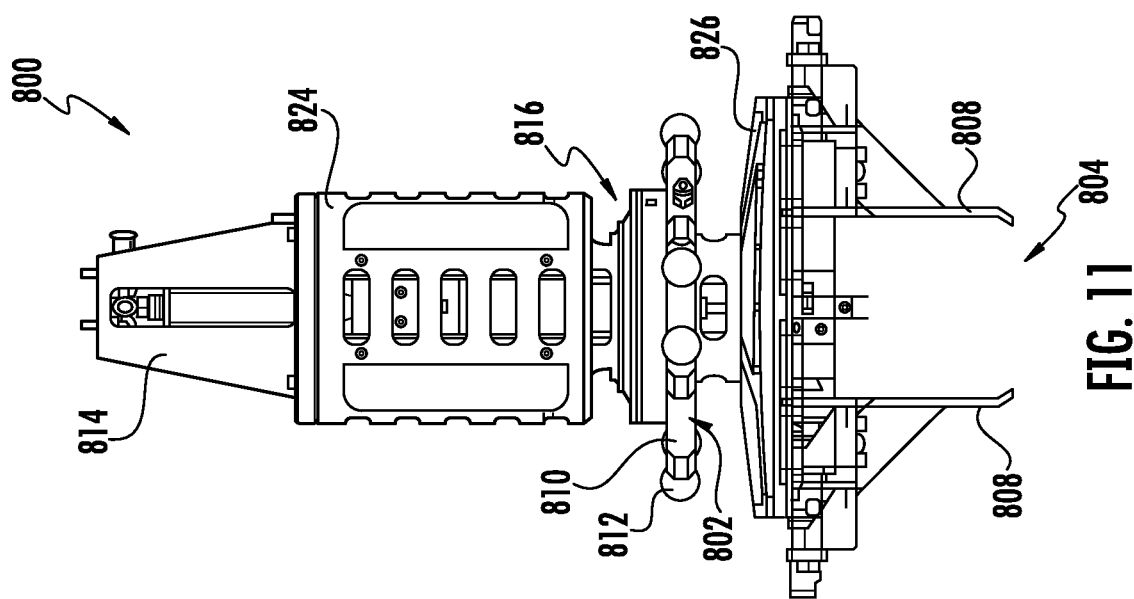
Figure 13:
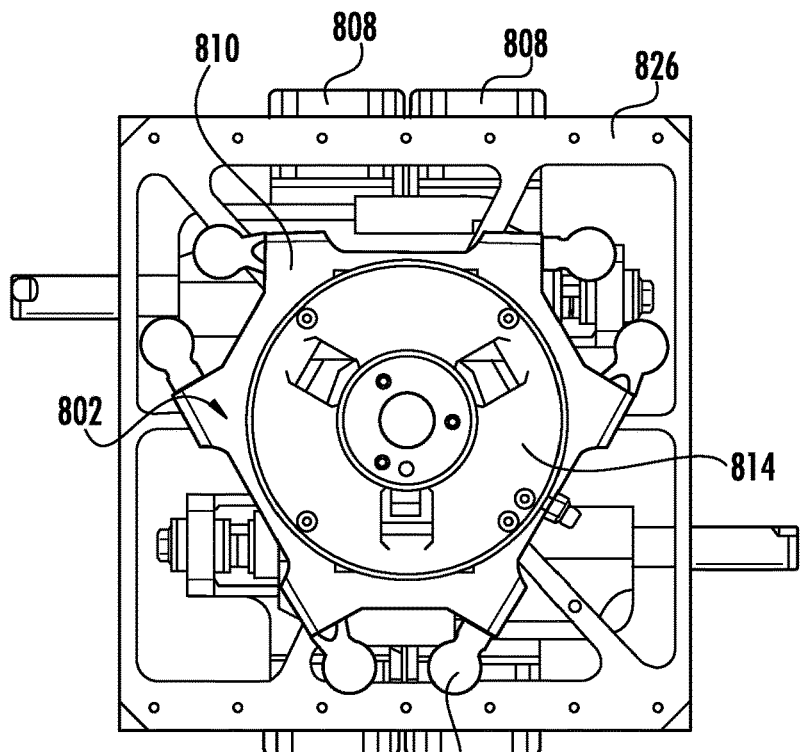
Figure 14:
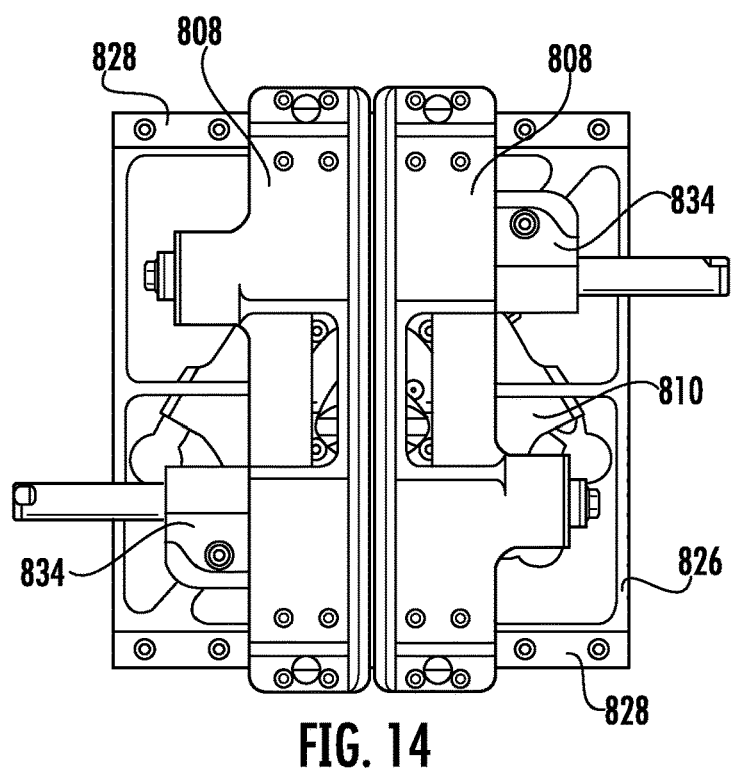
Figure 15:
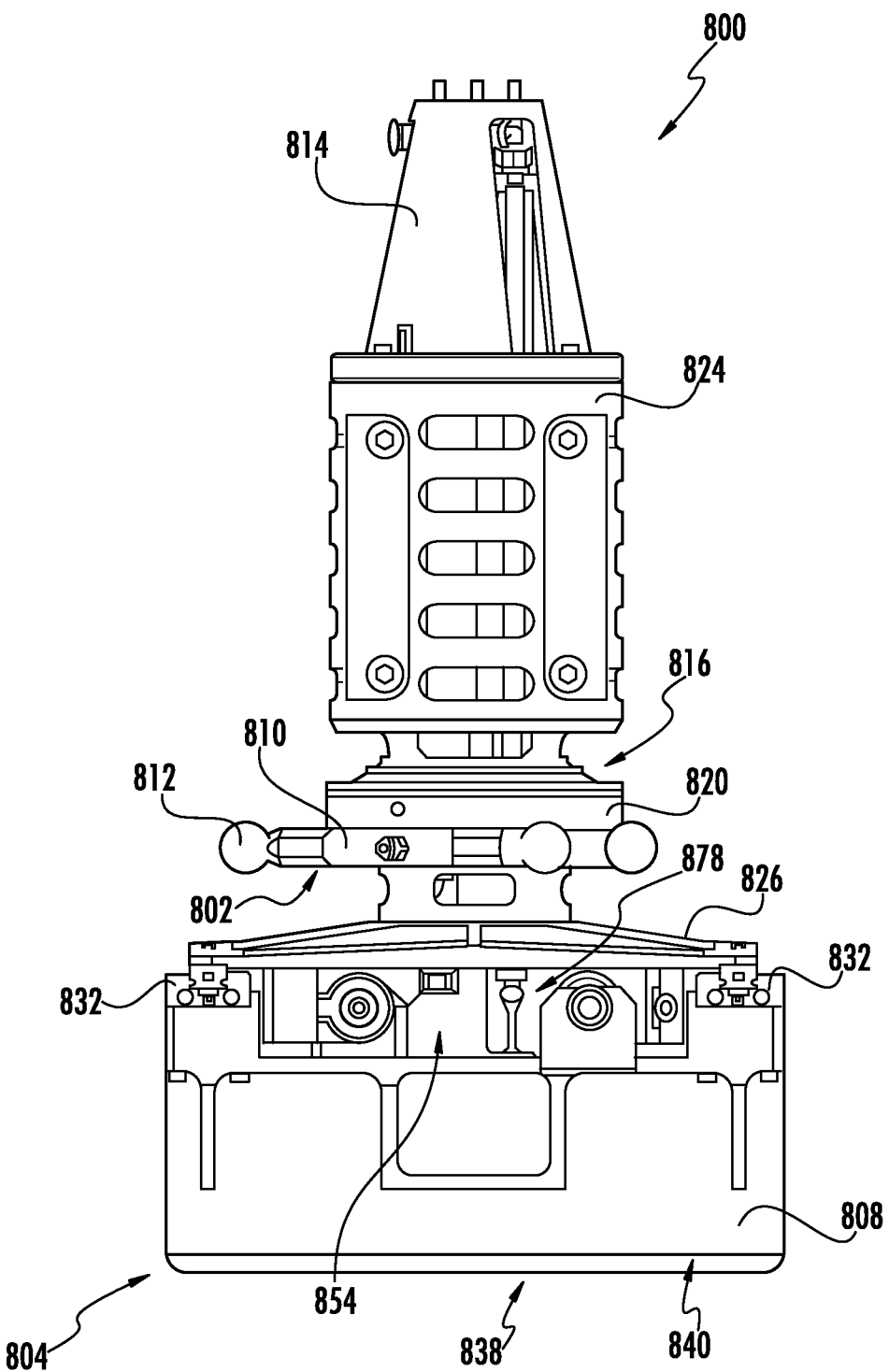
Figure 19:
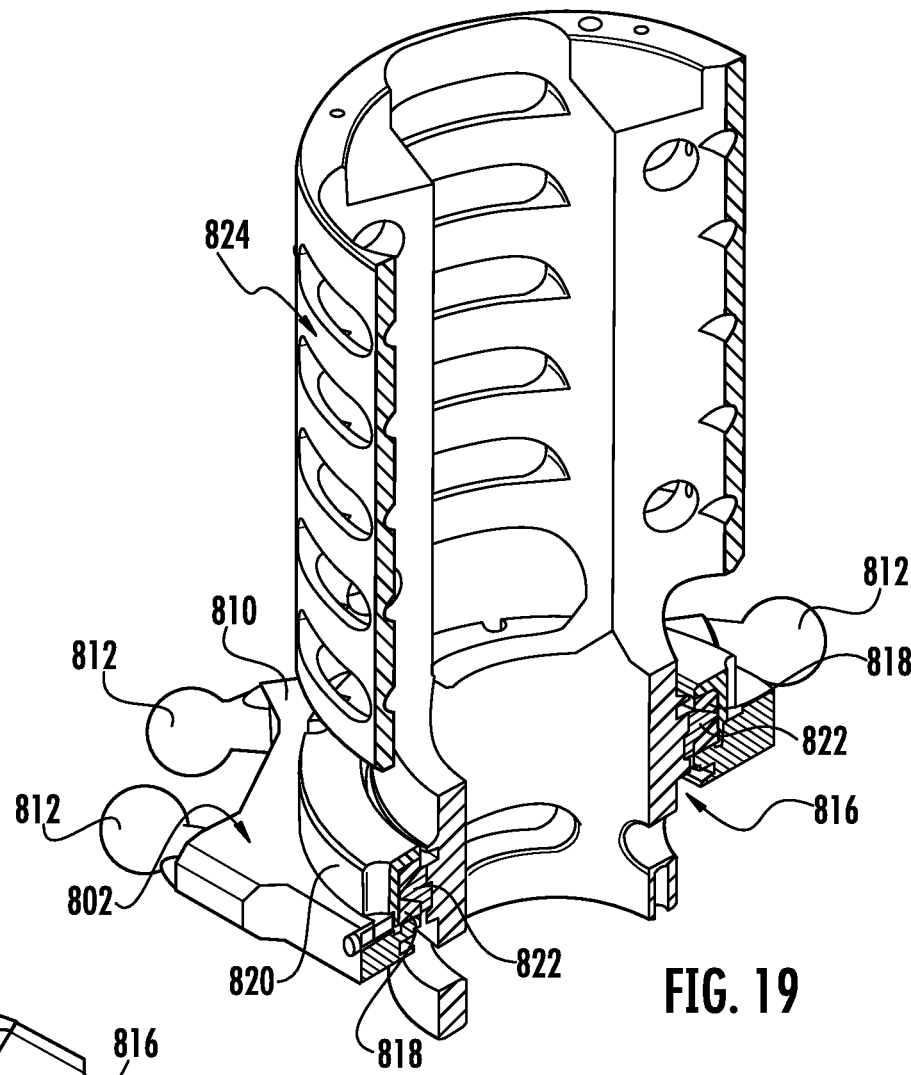
Figure 20:
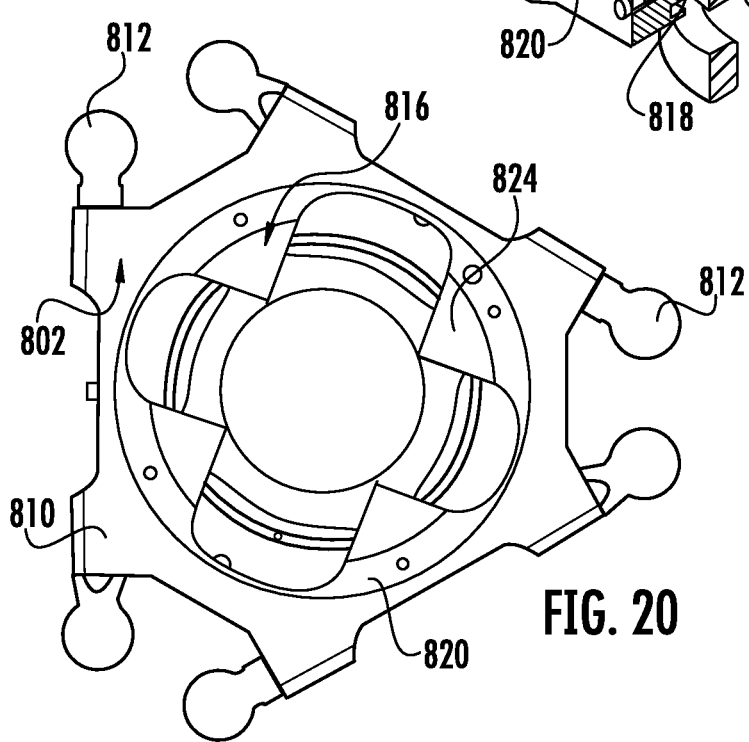
Figure 21:
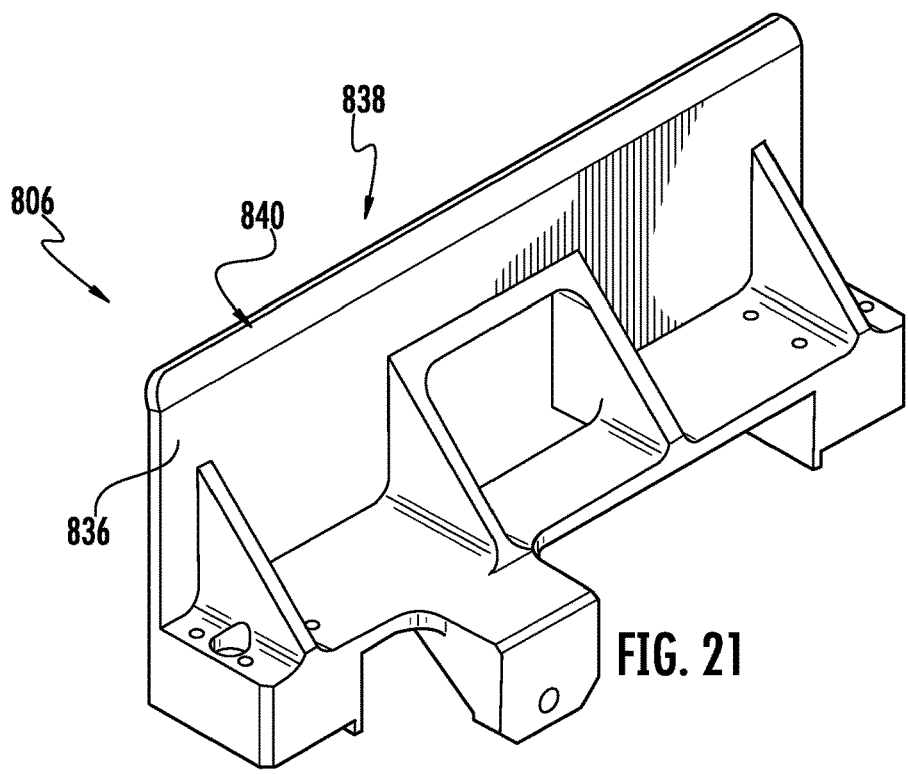
Figure 22:
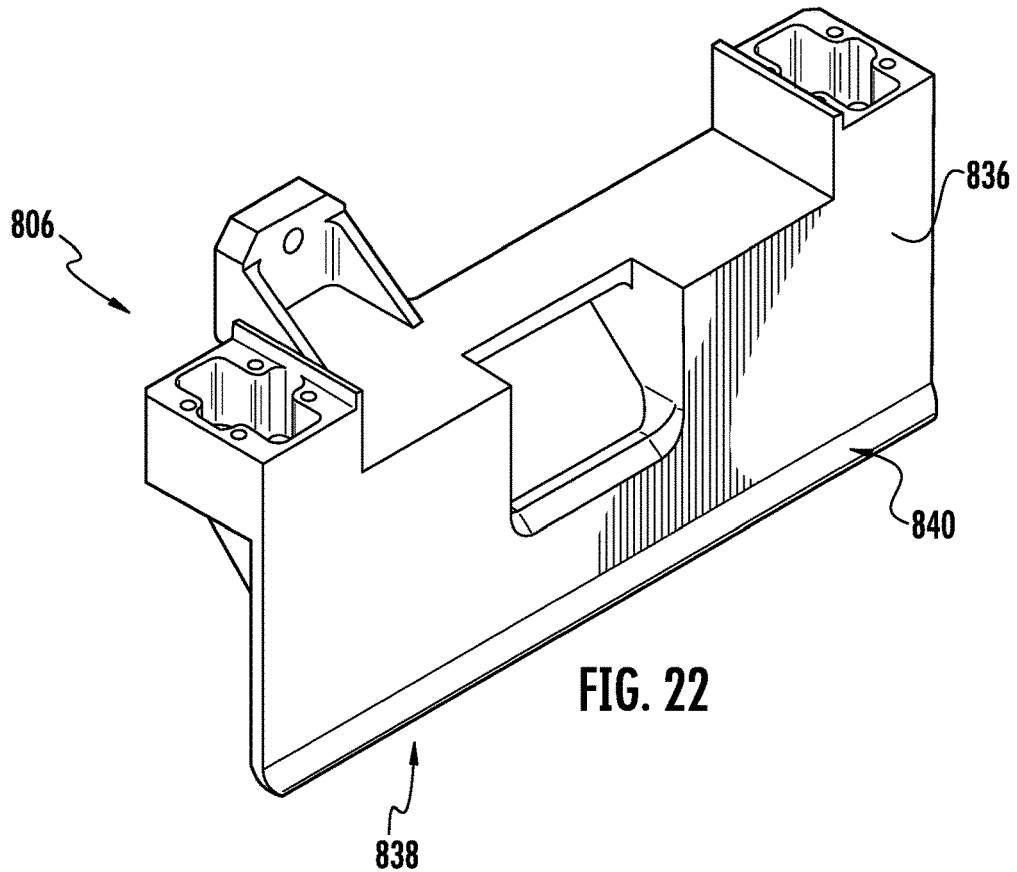
Figure 23:
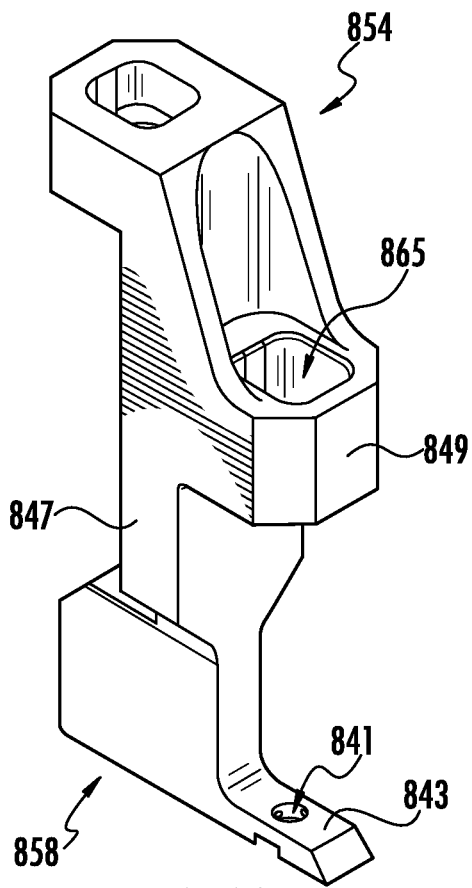
Figure 24:
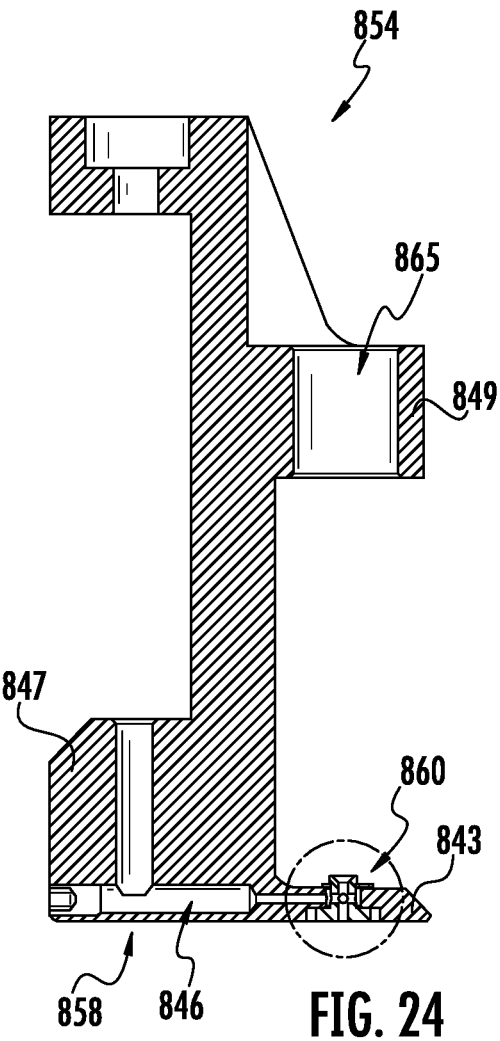
Figure 25:
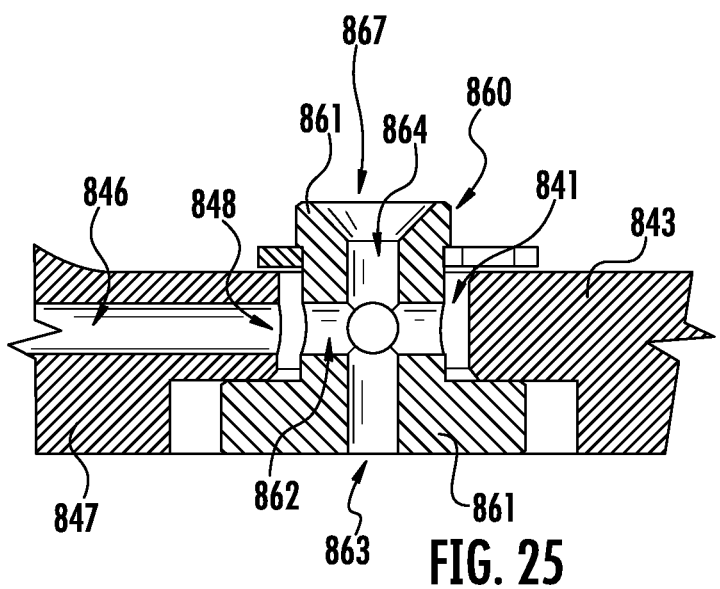
Figure 26:
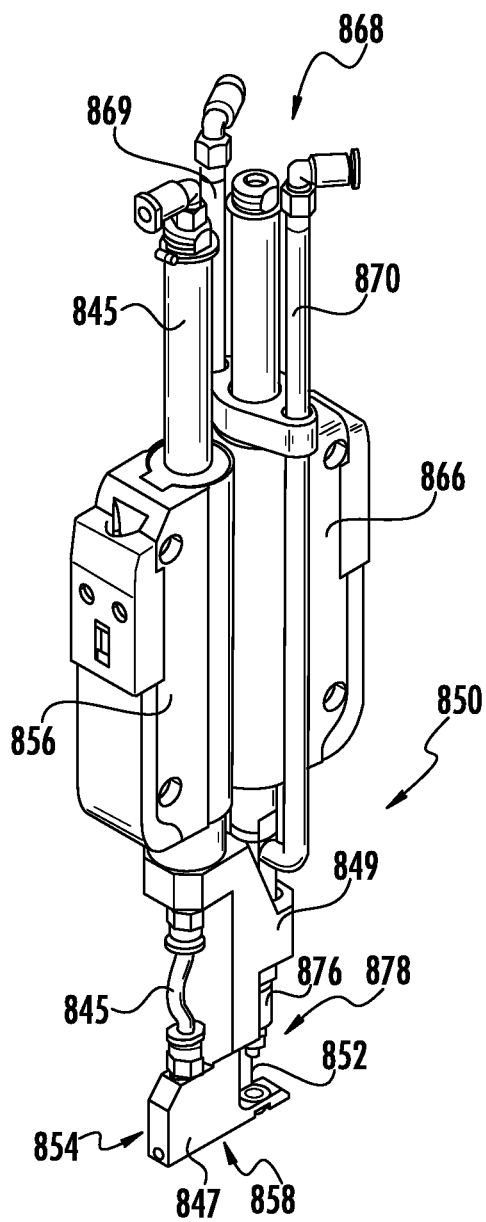
Figure 27:
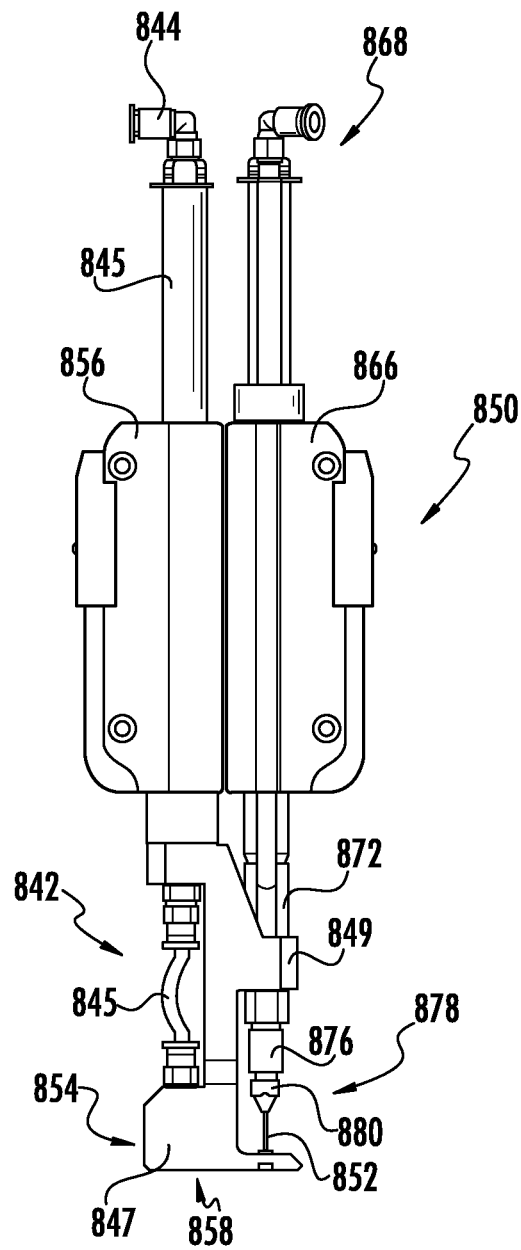
Figure 28:
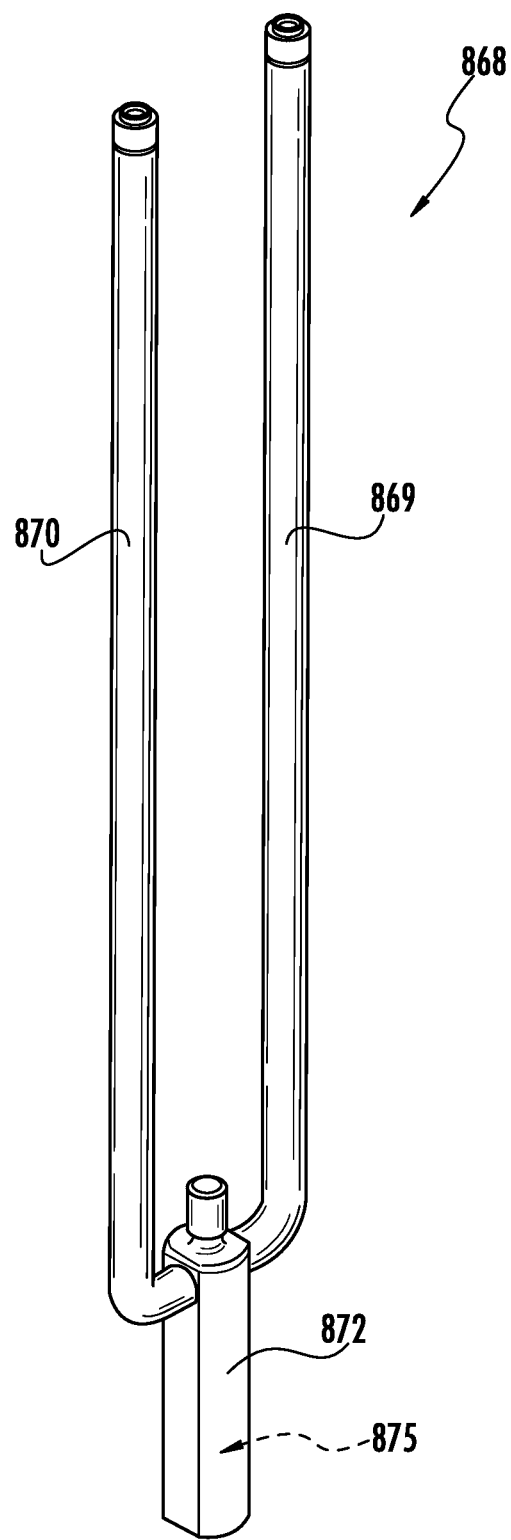
Figure 29:
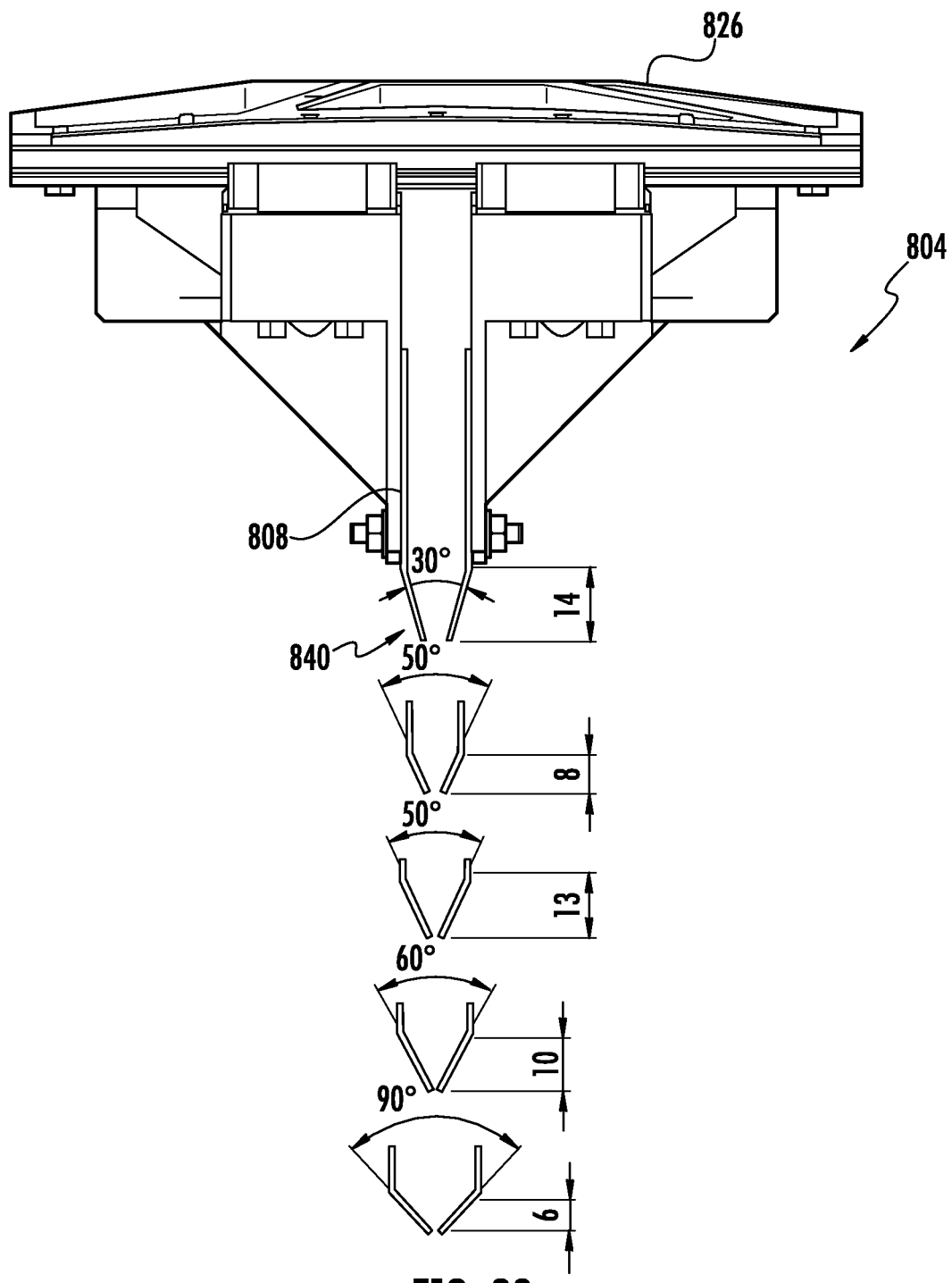
Figure 30:
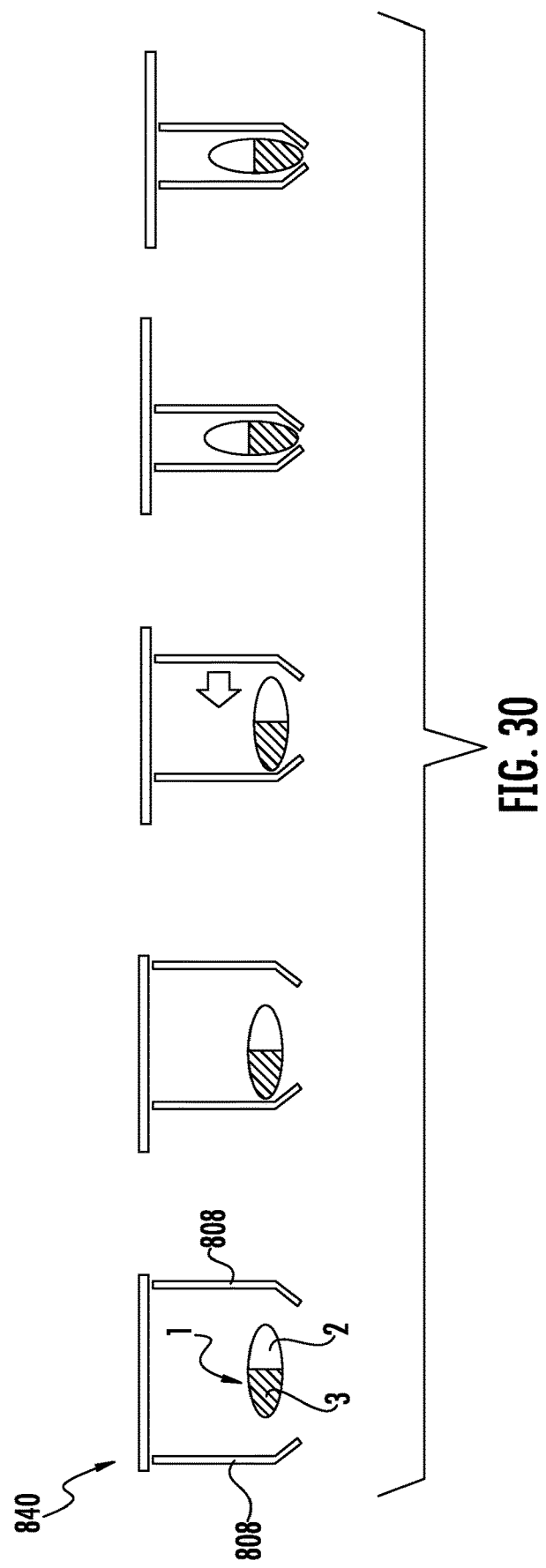
Figure 31:
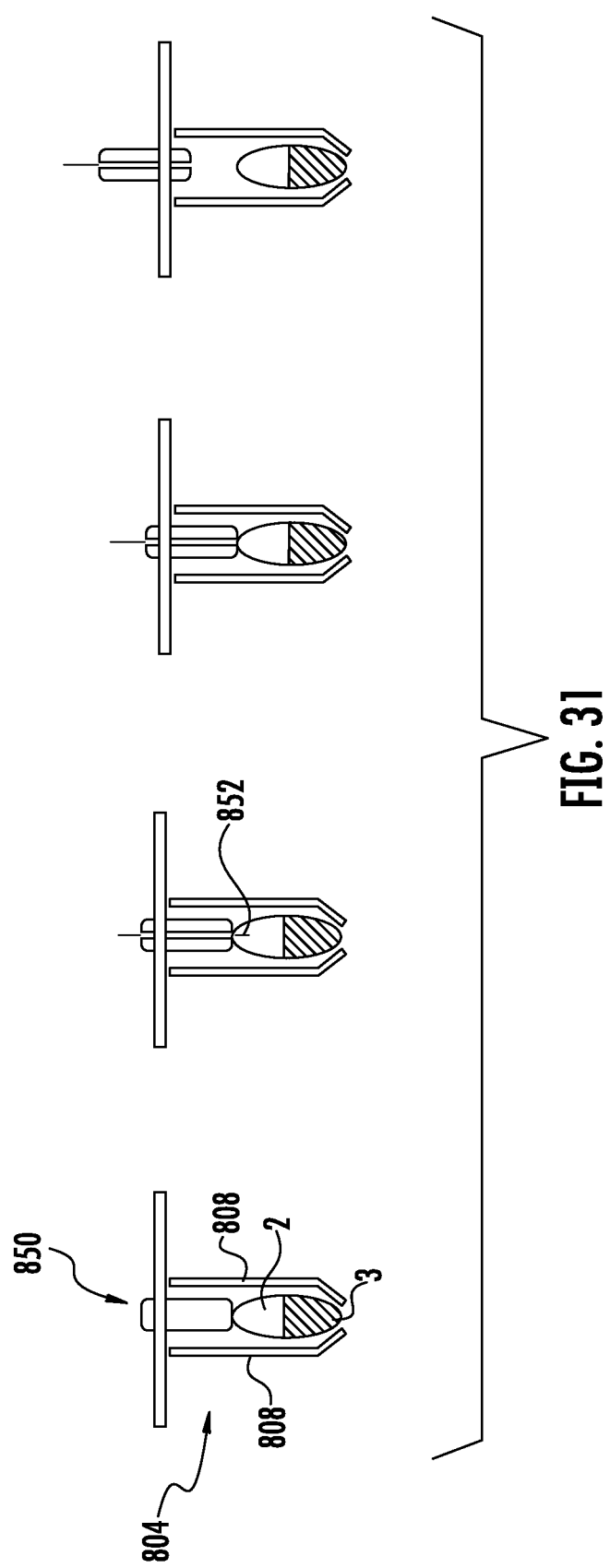

Having thus described various embodiments of the present disclosure in general terms, reference will now be made to the accompanying drawings, which are not necessarily drawn to scale, and wherein:

FIG. 1 is a perspective schematic view of a fish processing system, according to various aspects of the present disclosure;

FIG. 2 is a partial perspective schematic view of a fish processing system having a fish inspection unit, according to one aspect of the present disclosure;

FIG. 3 is a partial perspective schematic view of a fish processing system having a fish handling unit, according to one aspect of the present disclosure;

FIG. 4 is a perspective schematic view of a fish handling unit having a robotic cell capable of interacting with live fish transported on a conveyor, according to one aspect of the present disclosure;

FIG. 5 is a perspective schematic view of a sorting unit for sorting fish post-vaccination according to predetermined parameters, according to one aspect of the present disclosure;

FIG. 6 is a perspective schematic view of a fish handling unit having a robotic cell with an end effector capable of picking up a live fish oriented in any direction, according to one aspect of the present disclosure;

FIG. 7 is a perspective schematic view of a fish handling unit having a robotic cell with an end effector capable of rotating a live fish once lifted from a conveyor, according to one aspect of the present disclosure;

FIGS. 8 and 9 are perspective schematic views illustrating a sequence in which a robotic cell having an end effector picks up a live fish from a conveyor, according to one aspect of the present disclosure;

FIG. 10 is a perspective schematic view of an end effector for implementation on a robotic cell, the end effector being capable of picking up and vaccinating a live fish, according to one aspect of the present disclosure;

FIG. 11 is a schematic front view of the end effector of FIG. 10, illustrating a gripper assembly in a fully open position;

FIG. 12 is a schematic front view of the end effector of FIG. 10, illustrating a gripper assembly in a fully closed position;

FIG. 13 is a schematic top view of the end effector of FIG. 10;

FIG. 14 is a schematic bottom view of the end effector of FIG. 10, with the gripper assembly in a fully closed position;

FIG. 15 is a schematic side view of the end effector of FIG. 10;

FIGS. 16-18 are cross-sectional side views of the end effector of FIG. 10, illustrating a pusher and needle assembly thereof at various positions;

FIG. 19 is a cross-sectional schematic perspective view of a housing connected to a wrist section of the end effector of FIG. 10;

FIG. 20 is a top schematic view of a housing connected to a wrist section of the end effector of FIG. 10;

FIGS. 21 and 22 are perspective schematic views of a gripper blade of the end effector of FIG. 10;

FIG. 23 is a perspective schematic view of a pusher of the end effector of FIG. 10;

FIG. 24 is a cross sectional view of the pusher of FIG. 23;

FIG. 25 is a magnified view of the circled section of the pusher in FIG. 24;

FIGS. 26 and 27 are various schematic views of an injection assembly of the end effector of FIG. 10;

FIG. 28 is a perspective schematic view of a fluid assembly of the end effector of FIG. 10;

FIG. 29 is a schematic view of various embodiments of a gripper assembly for use in orienting a fish in a desired position, according to various aspects of the present disclosure;

FIG. 30 illustrates a fish orienting sequence, according to one aspect of the present disclosure; and FIG. 31 illustrates a fish vaccination sequence once gripped by a gripper assembly, according to one aspect of the present disclosure.

DETAILED DESCRIPTION OF THE DISCLOSURE

Various aspects of the present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

The apparatuses and methods of the present disclosure will now be described with reference to the figures. With initial reference to FIG. 1, illustrated is an exemplary fish processing system 100 for processing live, but anesthetized/sedated, fish. The fish processing system 100 may have any number of modules, sub-systems or units capable of interacting with one another to process live fish in an automated manner. For example, the fish processing system 100 may include a buffer unit 200, an anesthetizer unit 300, a transporter unit 400 and a fish handling unit 500.

Live fish may first be delivered through a pipeline 110 to the buffer unit 200 having a buffer tank 210 filled with water. A rotatable platform (not shown) may be rotated through the buffer tank 210 to lift fish therefrom and deliver them to an anesthetizer tank 310 of the anesthetizer unit 300. Water in the anesthetizer tank 310 includes an anesthetic medicament for sedating the fish. The anesthetizer unit 300 may also include a rotatable platform 320 for delivering the sedated fish to a duct 350 with flowing water. The fish are delivered by the duct 350 to the transporter unit 400 for singulation and/or separation thereof for handling. The transporter unit 400 may include an endless belt 410 having a plurality of slats 420 oriented transversely to the direction of travel of the endless belt 410. The slats 420 may be used to transport the fish to an elevated position to aid in singulation and/or separation thereof.

As shown in FIG. 2, the transporter unit 400 may have a plurality of dividers 430 forming multiple lanes through which the fish 1 individually move so as to be delivered in a separated fashion to the fish handling unit 500. A conveyor assembly 550 having one or more conveyor segments 555 may be provided for moving the fish 1 through the fish handling unit 500. The conveyor assembly 550 may be formed of one or more endless belts 560. An inspection system 600 may be provided for inspecting the sedated fish 1 for defects. In addition, the inspection system 600 may measure various features of the fish, such as fork length and size. Based on these measurements, an estimated weight of each fish may be determined by a processor. Such information may be used to target a desired injection point on the fish, as will be discussed in further detail.

In some instances, the inspection system 600 may include an image capture or vision system for optically scanning the fish as they move along the conveyor assembly 550. According to some aspects, the conveyor assembly 550 may include a gap 570 between two conveyor segments 555, with a first image capture device 610 positioned above the gap 570 and a second image capture device 620 positioned below the gap 570, underneath the conveyor assembly 550. Using the first and second image capture devices 610, 620, a three-dimensional representation of each fish may be created, regardless of orientation of the fish on the conveyor assembly 550. In this regard, both sides of the fish may be imaged such that morphological defects can be visually detected. The second image capture device 620 captures snippets of the fish as it passes over the gap 570, which can be integrated or stitched together with a processor having image processing algorithms so as to image the side of the fish that is against the conveyor assembly 550.

The inspection system 600 is in communication with a controller for controlling various aspects of thereof, including the ability to instruct the inspection system 600 and other components of the fish handling unit 500. The visual information processed by the processor may be communicated to the controller for processing of the fish as described further herein.

As shown in FIG. 3, the fish handling unit 500 may have a frame 502 for supporting the conveyor assembly 550. In some instances, one or more sections of the fish handling unit 500 may be enclosed within a cabinet (not shown) connected to the frame 502. The frame 502 may include a gantry 504 from which one or more robotic cells 510 depend, extending toward the conveyor assembly 550 so as to be capable of interacting with fish conveyed thereby. According to some aspects, the robotic cell 510 may be a parallel robot (also known as a delta robot, a spider robot, or a pick and place robot) provided, as a manipulator, with a parallel mechanism in which a base section 512 and a movable section 802 are interconnected by a movable-section drive mechanism 514 having a plurality of assembled-link structures 516 arranged to move in parallel, and has a configuration in which the movable section 802 performs a three-axis translational motion with respect to the base section 512 (i.e., the parallel robot is provided with a parallel mechanism having three degrees of freedom). Such a parallel robot is commercially available from Schneider Electric under the product name PacDrive Delta 3 robot (P4 robot). However, the present invention is not limited to such a configuration, but can also be applied to a configuration provided with a parallel mechanism having four or more degrees of freedom, in which the movable section 802 can perform a one, two or three-axis rotational motion with respect to the base section 512 in addition to the three-axis translational motion.

The movable-section drive mechanism 514 includes three assembled-link structures 516 arranged in parallel with each other, and three prime movers (or servo motors) for respectively driving the assembled-link structures 516. Each assembled-link structure 516 includes a driving link 518 articulately connected to the base section 512 and the output part of a corresponding prime mover through a plurality of revolute pairs and an auxiliary link, and a parallel pair of driven links 520 articulately connected at the distal end of the driving link 518 through a revolute pair. The parallel driven links 520 are articulately connected at the distal ends thereof to the movable section 802 through a revolute pair. More specifically, universal joints 812 are provided between the driving link 518 and the driven links 520, and also between the driven links 520 and the movable section 802.

In some instances, it may be desirable for the robotic cell 510 to be capable of providing rotational motion. Accordingly, the robotic cell 510 may include a wrist-section drive mechanism 525 operating to allow a wrist section 816, provided rotatably in the movable section 802, to perform a rotational motion with respect to the movable section 802. According to some aspects, the robotic cell 510 may be capable of allowing for a one, two or three-axis rotational motion. The wrist-section drive mechanism 525 may include a transmission member 530 (e.g., a rotatable shaft) formed as a monolithic or single-piece rod-shaped element.

The robotic cell 510 is in communication with the controller such that information received from the inspection system 600, such as size of the fish and position/orientation of the fish on the conveyor assembly 550, may be communicated to the robotic cell 510 and its orientation control algorithms. In this regard, the robotic cell 510 may be synchronized with the conveyor assembly 550 such that the robotic cell 510 is able to interact with the fish during continuous motion thereof on the conveyor assembly 550, thereby facilitating desired throughput. That is, the robotic cell 510 is able to accurately locate and engage each fish as it is transported along the conveyor assembly 550.

An end effector 800 may be provided for interacting with live fish moving on the conveyor assembly 550, such end effector 800 including the movable section 802 as a component thereof. As such, the robotic cell 510 may be capable of providing translational and/or rotational motion to the end effector 800. The robotic cell 510 is capable of moving the end effector 800 at desired speeds to attain a desired throughput. While the fish handling unit 500 shown in FIG. 3 includes three robotic cells 510, it is understood that any number of robotic cells 510 may be provided to meet desired throughput requirements, or for effecting various desired functions.

Referring now to FIG. 4, the end effector 800 may be capable of gripping the live fish 1, regardless of their orientation on the conveyor assembly 550, to lift them from the conveyor assembly 550 and then transfer the fish to an injection device 575. Since the end effector 800 is capable of rotation, the fish 1 may be in any orientation on the conveyor assembly 550, thus eliminating the need for physically demanding upstream processes and equipment for orienting the fish in a single direction. Because some fish (e.g., salmon, trout, sea bass) receive injections in the abdomen in a small targeted area (for example, about 1 cm in length for salmon) along the centerline thereof, the fish may be oriented by the end effector 800 in a desired orientation on the injection device 575. Since the end effector 800 is capable of rotation, the orientation of the fish on the conveyor assembly 550 is inconsequential, as the end effector 800 is able to rotate the fish to any orientation for placement on the injection device 575. After vaccination, the fish may be directed to a sorting unit 700, as shown in FIG. 5. The sorting unit 700 may include one or more chutes 710 for sorting the fish according to size, as determined by the inspection system 600. The chutes 710 may be capable of movement to align with one of a plurality of channels 720 defined by a fish removal system 730 flowing with water.

According to some aspects, the end effector 800 may be capable of injecting or sampling the fish as they move along the conveyor assembly 550. In this regard, some vaccines or other treatment fluids may be injected in target areas on the side of the fish, rather than the abdomen. In such instances, it may be desirable to simply leave the fish on the conveyor assembly 550 during the injection sequence, where the fish may be sorted at the end of the conveyor assembly 550 or with a subsequent robotic cell 510 with gripping capabilities. This may also be the case for withdrawing a sample from the fish as they move along the conveyor assembly 550. The extracted sample may be transferred from the end effector 800 to a sample receptacle for analysis. Once the sample is analyzed, the information may be communicated to a robotic cell 510 downstream for appropriate sorting. Thus, it is understood that the fish handling unit 500 may have robotic cells 510 having various end effectors 800 for interacting with the fish in a variety of ways.

In some instances, it may be desirable to combine the gripping and injection (or sampling) functions into a single end effector 800 in order to improve efficiencies and reduce the footprint of the fish handling unit 500, as shown in FIGS. 6-9 and 31. In this regard, it is unnecessary to move the fish to a separate injection device 575, but instead the end effector 800 is able to grip and lift the fish in a desired orientation, inject a treatment substance, and transport the fish to the sorting system 700. FIG. 7 illustrates rotation of the end effector 800 so that the fish can be delivered to the sorting system 700, according to one aspect. Typically, the target area for injection of the fish is not centered along the length of the abdomen, so the robotic cell 510 is capable of moving the end effector 800 to a position relative to the fish where the injection can occur at the target site, based on information received from the inspection system 600, regardless of orientation of the fish on the conveyor assembly 550. In this regard, the injection mechanism of the end effector 800 does not need to be laterally adjustable to inject the target area, although it could be so configured.

In instances where the abdomen of the fish is the target area for injection or sampling, the end effector 800 may be configured to orient the fish such that the abdomen is presented and accessible to the injection mechanism of the end effector 800, as shown in FIGS. 8 and 9. The end effector 800 may have a gripper assembly 804 with a plurality of engagement members 806 cooperating to orient and grip the fish for injection and transport. As shown, the engagement members 806 may be formed of a pair of gripper blades 808 capable of moving toward and away from one another to grip and release the fish. The opposing gripper blades 808 may cooperate to orient the fish such that the abdomen is facing upward to make the target site thereon accessible to the injection or sampling means.

Referring now to FIGS. 10-28, an exemplary end effector 800 and associated components for integrating the gripping and injection (or sampling) functions are illustrated. The end effector 800 includes the movable section 802 for translational and rotational motion by the robotic cell 510. The movable section 802 may include a parallel plate 810 having a plurality of joints 812 configured to connect to the assembled-link structures 516 so as to be capable of facilitating translational motion of the end effector 800. A cap 814 of the end effector 800 may be connected with appropriate fasteners to the transmission member 530 for facilitating rotational motion via the wrist section 816, which is provided rotatably in the movable section 802. The wrist section 816 may include a bearing ring 818, a bearing tension ring 820, and a bearing 822, as shown in FIG. 19. The wrist section 816 is rotatable with respect to the parallel plate 810. The wrist section 816 may be engaged with a housing 824 connected to the cap 814 such that rotation effected by the transmission member 530 is transferred to the wrist section 816.

The gripper assembly 804 may be connected to the wrist section 816 such that desired orienting thereof to mirror the orientation of the fish may be achieved. That is, the gripper blades 808 of the gripper assembly 804 may be positioned parallel to the longitudinal direction of the fish regardless of its orientation on the conveyor assembly 550. The gripper assembly 804 may include a main plate 826 connected to the housing 824 with appropriate fasteners such that the main plate 826 is also rotatable. A pair of side rails 828 may be engaged with the main plate 826 on opposite sides thereof. The side rails 828 define a bearing channel 830 configured to receive a bearing device 832 such that the bearing device 832 may be slidably moved along the respective side rail 828. A pair of the bearing devices 832 may be connected to each gripper blade 808 on opposite ends thereof such that the gripper blade 808 is also capable of slidably moving along the side rails 828 via the bearing devices 832. In this regard, the side rails 828 are oriented transverse to the gripper blades 808. FIG. 11 illustrates the gripper blades 808 in a fully open position, while FIG. 12 illustrates a fully closed position.

The gripper assembly 804 may further include a pair of gripper actuators 834 such as linear actuators for facilitating movement of the gripper blades 808 in order to accomplish the gripping function. Each gripper blade 808 has a respective gripper actuator 834 associated therewith such that each gripper blade 808 may be independently controlled. Such independent control of each gripper blade 808 is useful, although not necessary, because such control may be used to ensure the flat-lying fish is rotated to the desired orientation, as illustrated in the sequence shown in FIG. 30. In this regard, upon positioning of the gripper assembly 804 proximate to the fish 1, the gripper blade 808 positioned adjacent the abdomen (non-shaded portion 2) may be moved at a faster speed than the other gripper blade 808 positioned adjacent the backbone side (shaded portion 3) of the fish 1, thereby causing the abdomen 2 to be engaged first and/or at a rate of speed so as to initiate rotation of the fish in an orientation in which the abdomen 2 is facing upwardly. Even though, in some instances, the gripper blade 808 positioned adjacent the backbone side 3 may be moved into a stabilizing position proximate to and/or in contact with the fish 1 prior to movement of the gripper blade 808 that will engage the abdomen 2. Thus, when the gripper blades 808 advance inwardly the fish may be further compressed to move in the desired orientation. For injection purposes, precise location of the gripper blades 808 in relation to the fish 1 is provided by the robotic cell 510 since the fish cannot be moved longitudinally within the gripper assembly 804 after being captured thereby.

It is understood, however, that the gripper blades 808 may be moved at the same rate of speed to accomplish satisfactory orienting of the fish as based on the external morphology thereof. It is further understood that the end effector 800, and hence the gripper assembly 804, may be tilted (rotated away from vertical) by the robotic cell 510 to assist in orientating the fish during the gripping sequence. Additionally, one of the gripper blades 808 may be initially positioned closer to the fish in order to get the desired flipping action of the fish.

Each gripper blade 808 may have a plate 836 (FIGS. 21 and 22) extending away from the main plate 826 so as to be substantially perpendicular thereto. In some instances, a distal end 838 of the plate 836 may have an angled section 840 to provide a scooping action underneath the fish, in cooperation with the rounded external morphology of the fish at the abdomen and at the opposite backbone region. FIG. 29 provides various examples of how the gripper blades 808 may be arranged for facilitating the fish orienting procedure. As shown, the portions of the gripper blades 808 contacting the fish may be varied in length and/or angle.

In some instances, the gripper blades 808 may self-adjust to a home position once the fish is captured by the gripper assembly 804 such that the fish is in the correct alignment for injection (or sampling), as shown in FIG. 30. That is, the gripper assembly may be longitudinally aligned with the fish such that the gripper blades 808 are centered about the fish centerline. Because the gripper blades 808 may operate at varied speeds to ensure that the abdomen is oriented upwardly, the fish may be gripped off-center at an offset position. Thus, the gripper blades 808 may be moved to center the fish within the gripper assembly 804, as shown in FIG. 30.

As shown in FIG. 31, the end effector 800 may include an injection (or sampling) assembly 850 for injecting a substance into the fish or for withdrawing a sample from the fish. While reference is made throughout to an injection assembly, it is understood that such assembly may also be used to extract a tissue or fluid sample from the fish. Because fish have tough scales and skin about their exterior, including the abdomen, it may be desirable to compress an area of the fish proximate to the target injection site so that an injection needle 852 penetrates the skin rather than merely pushing the fish away. In this regard, a pusher 854 may be provided to slightly compress the abdomen of the fish during injection so as to immobilize the target injection site. The pusher 854 may be engaged with a pusher actuator 856 such as a linear actuator for moving an end 858 of the pusher 854 into contact with the fish. The amount of pressure to be applied by the pusher 854 may be adjusted on the fly by the pusher actuator 856 based on the size of the fish.

In some instances, the pusher 854 may also house a cleaning assembly 842 provided to clean fish scales or other debris from the injection needle 852. A cleaning fluid connector 844 may be connected to a reservoir containing a cleaning fluid (e.g., water). Tubing 845 is in fluid connection between the cleaning fluid connector 844 and a fluid channel 846 defined by a pusher body 847. The fluid channel 846 terminates at an exit port 848. A needle guide insert 860 may be positioned within an orifice 841 defined by an arm 843 extending from the pusher body 847. An insert body 861 of the needle guide insert 860 may define first and second insert channels 862, 864, which intersect within the insert body 861. The first insert channel 862 is in fluid communication with the fluid channel 846 such that cleaning fluid may be directed into the first and second insert channels 862, 864 for flushing debris from the injection needle 852, which moves longitudinally through the second insert channel 864 during an injection sequence. The insert body 861 may define a frustoconical inlet 867 and an outlet 863 through which the injection needle 852 extends and retracts. In this regard, upon retraction of the injection needle 852 within the insert body 861 (see FIG. 16), any debris (e.g., fish scales) present on the injection needle 852 may be dislodged therefrom mechanically. Extending from the pusher body 847 may be a guide support 849 defining a hole 865 for receiving the injection assembly 850.

The injection assembly 850 may extend through the housing 824 and be configured to deliver a treatment substance to the live fish, as particularly shown in FIGS. 16-18. FIG. 16 illustrates the injection assembly 850 in an idle position where the injection needle 852 is retracted within the needle guide insert 860. FIG. 17 illustrates the injection assembly 850 in position for injecting a relatively large fish, while FIG. 18 illustrates the position for a smaller fish. It is understood, however, that the injection assembly 850 is not limited to moving to these three illustrated positions, but instead is capable of adjusting to various injection positions based on the size of the fish as determined by the inspection system 600. FIG. 31 illustrates a sequence in which a fish 1 is gripped by the gripper assembly 804 and then the abdomen 2 engaged by the injection assembly 850 for injection by the injection needle 852, which is thereafter retracted.

As shown in FIGS. 26 and 27, an injection actuator 866 may be provided for moving the injection assembly 850 independently of the pusher 854. Such independent control of the injection assembly 850 may be used to adjust the penetration depth of the injection needle 852 into the fish based on the size thereof. That is, the injection assembly 850 may be configured to vary penetration of the injection needle 852 within the fish, rather than a fixed depth configuration, such that the treatment substance is delivered at a targeted depth based on fish size as determined by the inspection system 600. The injection assembly 850 may be capable of delivering one or more treatment substances (e.g., vaccines) to the fish. According to one aspect, the injection assembly 850 may include a fluid assembly 868 having a first fluid tubing 869 and a second fluid tubing 870, each in fluid communication with a respective pump system for transporting a treatment substance to the injection needle 852. Each pump system may be in fluid communication with a fluid reservoir containing the treatment substance (e.g., vaccine) to be delivered to the fish. As further shown in FIG. 28, the fluid assembly 868 may include a combining body 872 defining a combining chamber into which the first and second fluid tubing 869, 870 deliver the respective treatment substance. While the illustrated fluid assembly 868 shows two fluid tubing lines, it is understood that any number of treatment substances may be delivered by providing additional tubing.

A pneumatic line 874 may be connected for fluid communication with a combining chamber 875 defined by the combining body 872 such that air pressure may be applied to force the treatment substance out of the injection needle 852 for delivery to the target site, after penetration of the skin to a desired depth. A positive air supply may be in fluid communication with the pneumatic line 874 to provide a desired air pressure.

A needle adapter 876 may be provided for connecting a needle assembly 878 to the fluid assembly 868. The needle assembly 878 may include a hub 880 and the injection needle 852, which defines a cannula through which the treatment substance is passed. As previously discussed, the injection needle 852 may be adjusted to a desired depth based on the size of the fish as determined by the inspection system 600.

As previously mentioned, the exemplary end effector 800 shown in FIGS. 10-28 may be modified to provide an injection (or sampling) function only, by removing or otherwise rendering inoperable the gripper assembly 804. In this regard, the end effector 800 may be capable of moving about the conveyor assembly 550 to inject or sample fish with targeted precision based on information received from the inspection system 600.

Many modifications and other aspects of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. A fish handling unit, comprising:
   a frame having a gantry;
   an inspection system configured to inspect a plurality of live fish, identify a target site of injection, and determine size and orientation parameters of the live fish;
   a conveyor assembly configured to transport the live fish to the inspection system;
   at least one robotic cell depending from the gantry and extending toward the conveyor assembly, the robotic cell having a controller configured to control operation thereof, the controller being in communication with the inspection system; and
   an end effector operably engaged with the robotic cell, the end effector being configured to interact with the live fish moving along the conveyor assembly, based on parameters determined by the inspection system, wherein the end effector integrates a gripper assembly and an injection assembly into a single unit, the injection assembly being configured to inject the live fish with a treatment substance, wherein the injection assembly is configured to adjust the injection depth and location based on the size and orientation parameters provided by the inspection system, and the gripper assembly being configured to adjust a position of the live fish based on the determined orientation, the gripper assembly having a pair of opposing gripper blades configured to operate at varied speeds with respect to each other so as to cooperatively rotate the live fish so as to expose the target site of injection to the injection assembly.

2. A fish handling unit according to claim 1, wherein the robotic cell is configured to facilitate translational motion and rotational motion to the end effector.

3. A fish handling unit according to claim 2, wherein the end effector comprises a movable section operably engaged with the robotic cell for translational motion, and the end effector having a wrist section rotatable with respect to the movable section and operably engaged with the robotic cell for rotational motion.

4. A fish handling unit according to claim 1, wherein the gripper blades are individually and independently controlled by respective gripper actuators.

5. A fish handling unit according to claim 1, wherein the end effector further comprises a pusher individually controllable, with respect to the injection assembly, to apply compression to the live fish during an injection event.

* * * * *